US010743752B2

(12) United States Patent
On

(10) Patent No.: US 10,743,752 B2
(45) Date of Patent: Aug. 18, 2020

(54) ENDOSCOPE SYSTEM, CAPSULE ENDOSCOPE DEVICE, AND METHOD FOR OPERATING ENDOSCOPE SYSTEM

(71) Applicant: OLYMPUS CORPORATION, Hachioji-shi, Tokyo (JP)

(72) Inventor: Seigo On, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 385 days.

(21) Appl. No.: 15/836,681

(22) Filed: Dec. 8, 2017

(65) Prior Publication Data
US 2018/0098689 A1 Apr. 12, 2018

Related U.S. Application Data

(63) Continuation of application No. PCT/JP2015/067330, filed on Jun. 16, 2015.

(51) Int. Cl.
A61B 1/00 (2006.01)
A61B 1/04 (2006.01)
A61B 1/045 (2006.01)

(52) U.S. Cl.
CPC .......... A61B 1/041 (2013.01); A61B 1/00006 (2013.01); A61B 1/00016 (2013.01); A61B 1/00032 (2013.01); A61B 1/00036 (2013.01); A61B 1/045 (2013.01)

(58) Field of Classification Search
None
See application file for complete search history.

(56) References Cited

U.S. PATENT DOCUMENTS

| 6,709,387 | B1 | 3/2004 | Glukhovsky et al. |
| 2005/0158246 | A1 | 7/2005 | Takizawa et al. |
| 2010/0152534 | A1* | 6/2010 | Kim ...................... A61B 1/041 600/109 |
| 2013/0035547 | A1* | 2/2013 | Jung .................. A61B 1/00036 600/109 |

(Continued)

FOREIGN PATENT DOCUMENTS

| JP | 2004313242 A | 11/2004 |
| JP | 2005103130 A | 4/2005 |

(Continued)

OTHER PUBLICATIONS

International Search Report (ISR) and Written Opinion dated Sep. 15, 2015 issued in International Application No. PCT/JP2015/067330.

Primary Examiner — Timothy J Neal
(74) Attorney, Agent, or Firm — Holtz, Holtz & Volek PC

(57) ABSTRACT

An endoscope system includes a first capsule endoscope device and a second capsule endoscope device. The first capsule endoscope device is introduced into a living body before the second capsule endoscope device is introduced. The first capsule endoscope device includes a first image sensor and a first processor that controls an imaging operation by the first image sensor. The second capsule endoscope device includes a second image sensor and a second processor that performs a change process for control on an imaging operation by the second image sensor based on first information on the first capsule endoscope device.

14 Claims, 17 Drawing Sheets

(56) References Cited

U.S. PATENT DOCUMENTS

| | | | | |
|---|---|---|---|---|
| 2015/0283370 A1* | 10/2015 | Chae | ............ | A61N 7/00 |
| | | | | 600/109 |
| 2016/0220828 A1* | 8/2016 | Yan Poon | ............ | A61B 5/14503 |
| 2019/0281258 A1* | 9/2019 | Makino | ............ | A61B 1/00 |

FOREIGN PATENT DOCUMENTS

| | | |
|---|---|---|
| JP | 2006061399 A | 3/2006 |
| JP | 2006223892 A | 8/2006 |

\* cited by examiner

ENDOSCOPE SYSTEM, CAPSULE ENDOSCOPE DEVICE, AND METHOD FOR OPERATING ENDOSCOPE SYSTEM

CROSS REFERENCE TO RELATED APPLICATION

This application is a continuation of International Patent Application No. PCT/JP2015/067330, having an international filing date of Jun. 16, 2015, which designated the United States, the entirety of which is incorporated herein by reference.

BACKGROUND

Capsule endoscope devices are small and thus can only incorporate a battery with a limited capacity. Thus, power saving is required for capturing images in a long digestive tract. For example, JP-A-2006-223892 discloses a method for controlling a frame rate to achieve the power saving. In JP-A-2006-223892, at least two images captured in time series are compared with each other to measure the movement of the capsule endoscope device. The imaging frame rate is changed to be low when the movement of the capsule endoscope device is determined to be relatively slow, and is changed to be high when the movement of the capsule endoscope device is determined to be relatively fast.

SUMMARY

According to one aspect of the invention, there is provided an endoscope system comprising:
a first capsule endoscope device; and
a second capsule endoscope device,
the first capsule endoscope device being introduced into a living body before the second capsule endoscope device is introduced and including:
a first image sensor; and
a first processor that controls an imaging operation by the first image sensor,
the second capsule endoscope device including:
a second image sensor; and
a second processor that performs a change process for control on an imaging operation by the second image sensor based on first information on the first capsule endoscope device.

According to another aspect of the invention, there is provided a capsule endoscope device comprising:
an image sensor; and
a processor that controls an imaging operation by the image sensor,
the capsule endoscope device being settable to be in a first operation mode and in a second operation mode,
the processor performing, when the capsule endoscope device is set to be in the second operation mode, a change process for control on the image operation by the image sensor, based on first information on a capsule endoscope device that has been introduced into the living body before the capsule endoscope device set to be in the second operation mode is introduced, and has been set to be in the first operation mode.

According to another aspect of the invention, there is provided an endoscope system comprising:
a first capsule endoscope device;
a second capsule endoscope device; and
a processing device that performs a process of presenting introduction determination information for determining whether or not to introduce the second capsule endoscope device into the living body or determining an introduction timing, based on first information on the first capsule endoscope device that has been introduced into the living body before the second capsule endoscope device is introduced.

According to another aspect of the invention, there is provided a method for operating an endoscope system, the method comprising:
introducing a first capsule endoscope device into a living body, the first capsule endoscope device including a first image sensor and a first processor that controls an imaging operation by the first image sensor;
introducing a second capsule endoscope device into the living body, the second capsule endoscope device including a second image sensor and a second processor that controls an imaging operation by the second image sensor,
the second processor performing a change process for control on the imaging operation by the second image sensor, based on first information on the first capsule endoscope device.

DESCRIPTION OF EXEMPLARY EMBODIMENTS

Figure 1:
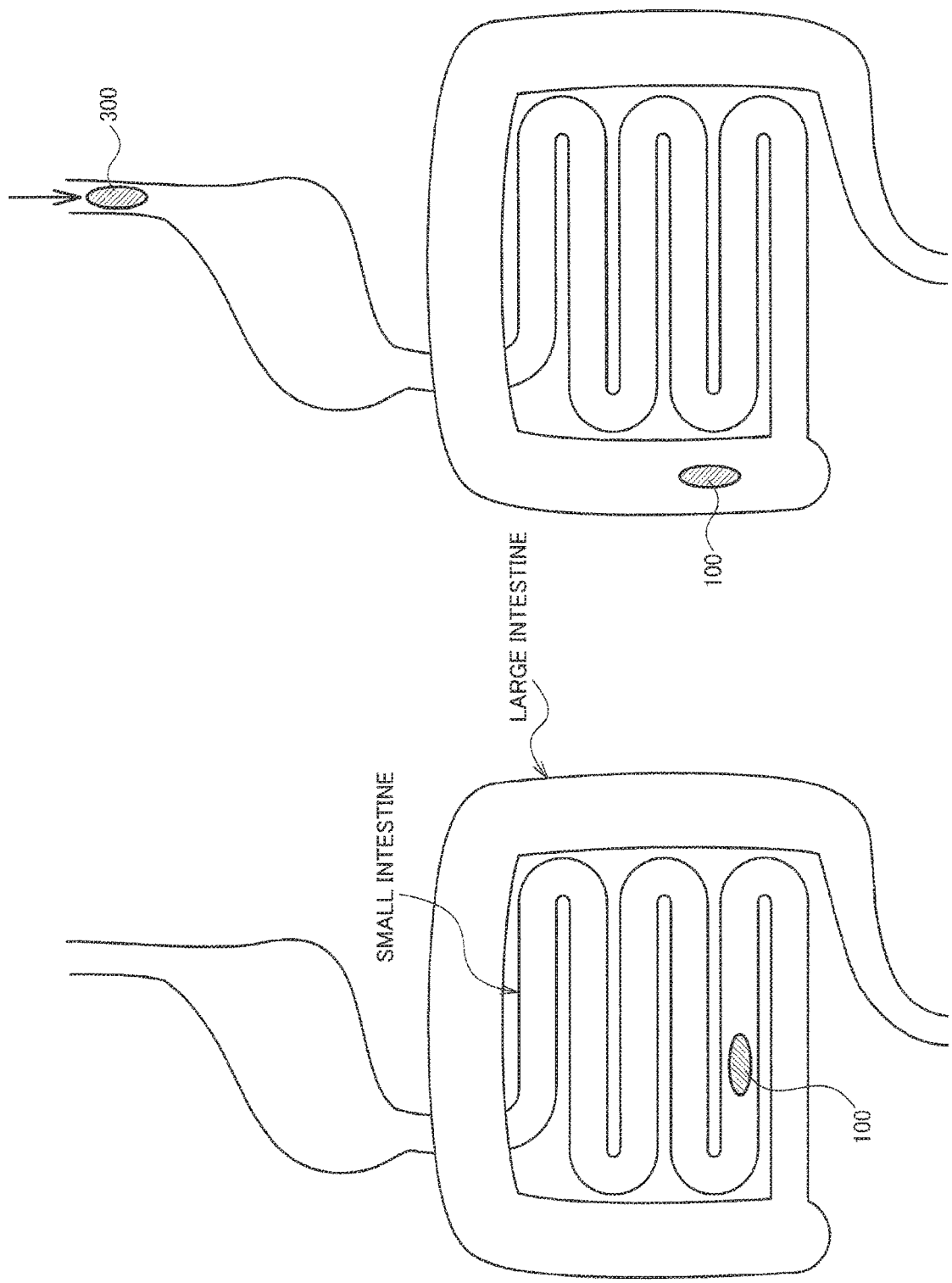
FIG. 1 illustrates imaging in a relay system.

Capsule endoscope devices have a risk of running out of battery while imaging is still in process, resulting in insufficient diagnosis. For example, in JP-A-2006-223892, an imaging frame rate is adaptively controlled with the movement of a capsule endoscope device measured through real-time comparison between two images for a long period of time after a capsule endoscope has been swallowed by a patient and before the capsule endoscope is excreted. Thus, an extremely large amount of images is captured, and thus a capsule internal battery might run out while the imaging is still in process.

Some aspects of the present embodiment can provide an endoscope system, a capsule endoscope device, a method for operating an endoscope system, and the like with which a risk of insufficient imaging due to discharged battery can be reduced.

According to one embodiment of the invention, there is provided an endoscope system comprising:

a first capsule endoscope device; and a second capsule endoscope device, the first capsule endoscope device being introduced into a living body before the second capsule endoscope device is introduced and including:

a first image sensor; and a first processor that controls an imaging operation by the first image sensor, the second capsule endoscope device including:

a second image sensor; and a second processor that performs a change process for control on an imaging operation by the second image sensor based on first information on the first capsule endoscope device.

According to one aspect of the present embodiment, the change process on the control for the imaging operation by the second image sensor of the second capsule endoscope device is performed based on the first information on the first capsule endoscope device introduced into the living body before the second capsule endoscope device is introduced. With this configuration, relay imaging can be performed with the first and the second capsule endoscope devices, whereby a risk of insufficient imaging due discharged battery can be reduced.

The exemplary embodiments of the invention are described below. Note that the following exemplary embodiments do not in any way limit the scope of the invention laid out in the claims. Note also that all of the elements described below in connection with the exemplary embodiments should not necessarily be taken as essential elements of the invention.

1. First Embodiment

For example, the digestive tract has parts including the stomach, the duodenum, the small intestine, and the large intestine. Among these, the small intestine is difficult to observe with a scope-type endoscope. Thus, a capsule endoscope device has conventionally been used mainly for observing the small intestine. To reduce a load on a patient or the like, the capsule endoscope device is preferably used also for capturing images in the large intestine. Logically, when the images in the large intestine are to be further captured, longer imaging time is required than in a case where the images are captured in the small intestine only. Thus, the demand for power saving becomes even more difficult to satisfy.

As illustrated in FIG. 1, a capsule endoscope device 100, swallowed by a patient, captures images from the upper digestive tract. The potential duration of the imaging by the capsule endoscope device 100 is roughly determined by a battery capacity. Thus, for example, if the capsule endoscope device 100 moves slowly or stops in the middle of the process, the battery might run out while the capsule endoscope device 100 is still inside the small intestine or the large intestine. In such a case, images can be captured only for a part of a target range, resulting in insufficient diagnosis.

In view of this, the present embodiment uses two capsule endoscope devices 100 and 300 for a single capsule-endoscopy examination for a single patient using, to reduce a risk of insufficient diagnosis. Specifically, the examination proceeds as follows. The first capsule endoscope device 100 is swallowed by the patient and captures images inside the patient's body, and the second capsule endoscope device 300 is swallowed by the patient after a certain period of time elapses. With the two capsule endoscope devices 100 and 300 thus introduced into the patient's body with a time difference, the images inside the living body are captured by a relay system. This ensures an effect of preventing insufficient diagnosis due to discharged battery, which might occur when the examination is performed with a single capsule endoscope device 100.

Figure 2:
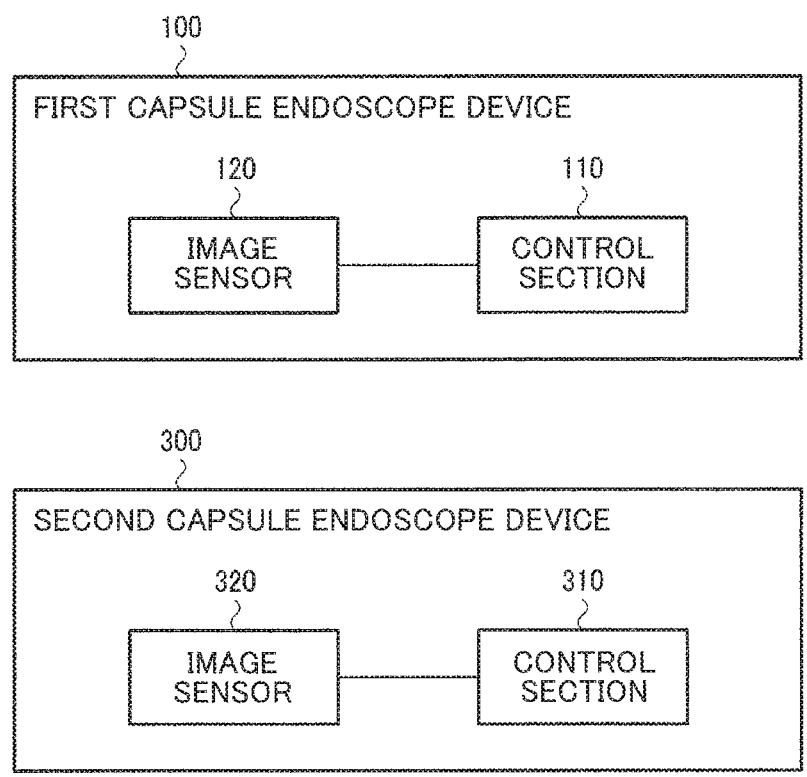
FIG. 2 illustrates an example of a configuration of an endoscope system according to a first embodiment.

FIG. 2 illustrates an example of a configuration of an endoscope system according to a first embodiment. The endoscope system includes the first capsule endoscope device 100 and the second capsule endoscope device 300.

The first capsule endoscope device 100 is introduced into the living body before (or together with) the second capsule endoscope device 300. The first capsule endoscope device 100 includes a first image sensor 120 and a first control section 110 (first controller) that controls an imaging operation by the first image sensor 120. The second capsule endoscope device 300 includes: a second image sensor 320; and a second control section 310 (second controller) that performs a change process for control on an imaging operation by the second image sensor 320 based on first information on the first capsule endoscope device 100.

With this endoscope system, images can be captured by the relay system using the two capsule endoscope devices 100 and 300, and thus can be captured over a wider range (for a longer period of time) than in a system using a single. This ensures prevention of a failure to capture images in the entire target imaging target range (resulting in insufficient diagnosis) due to the battery running out in the middle of the range. With the first information on the first capsule endoscope device 100, the second image sensor 320 can start the imaging operation (or have the frame rate switched) at an appropriate timing, whereby imaging can be appropriately relayed.

The first information may by any information on the first capsule endoscope device 100. Possible examples of the first information include: information generated or transmitted by the first capsule endoscope device 100; information on the characteristics of the first capsule endoscope device 100; information on the behavior of the first capsule endoscope device 100 in the living body; information on an operation performed on the first capsule endoscope device 100 by a user; information on time of the operation on the first capsule endoscope device 100 by the user (or time elapsed after the operation has been performed); information on time of any operation performed by the first capsule endoscope device 100 (or time elapsed after the operation has been performed); information on the position of the first capsule endoscope device 100; and information on time at which the first capsule endoscope device 100 has reached a predetermined position (or time elapsed after the position has been reached).

In the present embodiment, the second control section 310 performs the change process of starting the imaging operation of the second image sensor or switching a frame rate of the imaging operation of the second image sensor, in response to a trigger signal based on the first information.

The change process for the control on the imaging operation is not limited to that described above, and may be any process as long as power consumption by the second capsule endoscope device 300 before the change process is smaller than the power consumption by the second capsule endoscope device 300 after the change process.

For example, as described later with reference to FIG. 3 or the like, the endoscope system may include an extracorporeal device 200 that receives the first information from the first capsule endoscope device 100 and transmits the trigger signal, and the second control section 310 may perform the change process based on the trigger signal from the extracorporeal device 200. Alternatively, as described later with reference to FIG. 17 or the like, the second capsule endoscope device 300 may receive the first information from the first capsule endoscope device 100, and the second control section 310 (or a processing device in the second capsule endoscope device 300) may generate the trigger signal based on the first information.

With the trigger signal generated based on the first information as described above, the imaging operation by the second image sensor 320 can be started or performed with the frame rate switched. When the change process is performed in response to the trigger signal, the imaging is relayed to the second capsule endoscope device 300, whereby the image can be captured in the imaging target range after the battery of the first capsule endoscope device 100 runs out.

The first information according to the present embodiment is information on remaining battery charge of the first capsule endoscope device 100. Specifically, the first information is information indicating that the remaining battery charge of the first capsule endoscope device 100 has dropped to or below a predetermined amount.

Various methods may be employed for determining the remaining battery charge. For example, the power consumed from the battery may be counted, and the remaining battery charge may be determined to have dropped to or below the predetermined amount when the power consumption reaches a predetermined power amount. Alternatively, the remaining battery charge may be determined to have dropped to or below the predetermined amount when predetermined time has elapsed after the first capsule endoscope device 100 has started operating (turned ON). For example, the remaining battery charge may be a remaining amount of power or may be remaining operating time of the capsule endoscope device.

With the first information being the remaining battery charge information, the imaging by the second capsule endoscope device 300 can be controlled based on the remaining battery charge information. Thus, when the imaging cannot be continued by the first capsule endoscope device 100 due to low remaining battery charge, the imaging can be relayed to the second capsule endoscope device 300 and thus can be continued.

The first information according to the present embodiment is at least one of: an image captured by the first capsule endoscope device 100; information on time difference between the introduction of the first capsule endoscope device 100 into the living body and the introduction of the second capsule endoscope device 300 into the living body; and information on the position of the first capsule endoscope device 100 in the living body.

Various types of time difference information can be employed. For example, the time difference information may be information set in advance by a physician (stored in the extracorporeal device 200 or the second capsule endoscope device 300 illustrated in FIG. 3 for example). Alternatively, the time difference information may be information set by the physician when the second capsule endoscope device 300 is introduced (stored in the extracorporeal device 200 or the second capsule endoscope device 300 illustrated in FIG. 3 for example). Alternatively, predetermined time difference information may be set in advance. Furthermore, when the first capsule endoscope device 100 and the second capsule endoscope device 300 start, signals indicating the start of the devices may be transmitted to the extracorporeal device 200 (or the second capsule endoscope device 300), and the extracorporeal device 200 (or the second capsule endoscope device 300) may acquire the time difference information based on the signals.

With the image captured by the first capsule endoscope device 100 being the first information, the position of the first capsule endoscope device 100 in the living body can be determined based on the captured image. The imaging operation by the second capsule endoscope device 300 can be changed in accordance with the position. With the information indicating a time period between the introduction of the first capsule endoscope device 100 into the living body and the introduction of the second capsule endoscope device 300 into the living body being the first information, the imaging operation of the second capsule endoscope device 300 can be changed when the time period (or the time before or after the time period) elapses after the first capsule endoscope device 100 has been introduced into the living body.

The capsule endoscope device (capsule main body) according to the present embodiment may have the configuration described below. Specifically, the first capsule endoscope device 100 includes: a first memory that stores information (for example, a program and various types of data); and a first processor (a processor including hardware) that operates based on the information stored in the first memory. The second capsule endoscope device 300 includes: a second memory that stores information (for example, a program and various types of data); and a second processor (a processor including hardware) that operates based on the information stored in the second memory. The first processor performs a control process for controlling the imaging operation by the first image sensor 120. The second processor performs a second control process for performing the change process for the control on the imaging operation performed by the second image sensor 320, based on the first information on the first capsule endoscope device 100.

For example, the processors (the first and the second processors) may have functions of sections each implemented by individual hardware, or the functions of sections implemented by integrated hardware. For example, the processor includes hardware that may include at least one of a circuit that processes a digital signal and a circuit that processes an analog signal. For example, the processor may include one or a plurality of circuit devices (for example, an IC or the like) and one or a plurality of circuit elements (for example, a resistor, a capacitor, or the like) mounted on a circuit board. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an ASIC. The processor may include an amplifier circuit, a filter circuit, or the like that processes an analog signal. The memories (first, second memories) may be a semiconductor memory (e.g., SRAM or DRAM) or a register. For example, the memory may store a computer-readable instruction. A function of each section of the capsule endoscope device is implemented as a process when the processor executes the instruction. The sections of the capsule endoscope device include: the control section 110 and the control section 310 in FIG. 1; the control section 110, a captured image transmission section 103, an information transmission section 104, the control section 310, a captured image transmission section 303, and an information reception section 304 in FIG. 3, FIG. 14, and FIG. 15; and the control section 110, an image processing section 121, an analysis section 122, the information transmission section 104, the control section 310, an image processing section 321, an analysis section 322, a presentation section 324, and the information reception section 304 in FIG. 17. The instruction may be an instruction in an instruction set that is included in a program, or may be an instruction that causes a hardware circuit included in the processor to operate.

For example, operations according to the present embodiment are implemented as follows. The first processor outputs a control signal for controlling an imaging operation, and the first image sensor 120 performs the imaging operation based on the control signal. The second processor acquires the first information on the first capsule endoscope device 100, and generates a control signal for changing control on the imaging operation based on the first information. The second image sensor 320 changes the imaging operation based on the control signal.

The sections of the capsule endoscope device according to the present embodiment may be implemented as a module of a program that operates on the processor. For example, the first control section 110 is implemented as a first control module that performs a control process for controlling the imaging operation by the first image sensor 120. Similarly, the second control section 310 is implemented as a second control module that performs a second control process for performing the change process for the control on the imaging operation performed by the second image sensor 320, based on the first information on the first capsule endoscope device 100.

2. Second Embodiment 2.1. Endoscope System

Figure 3:
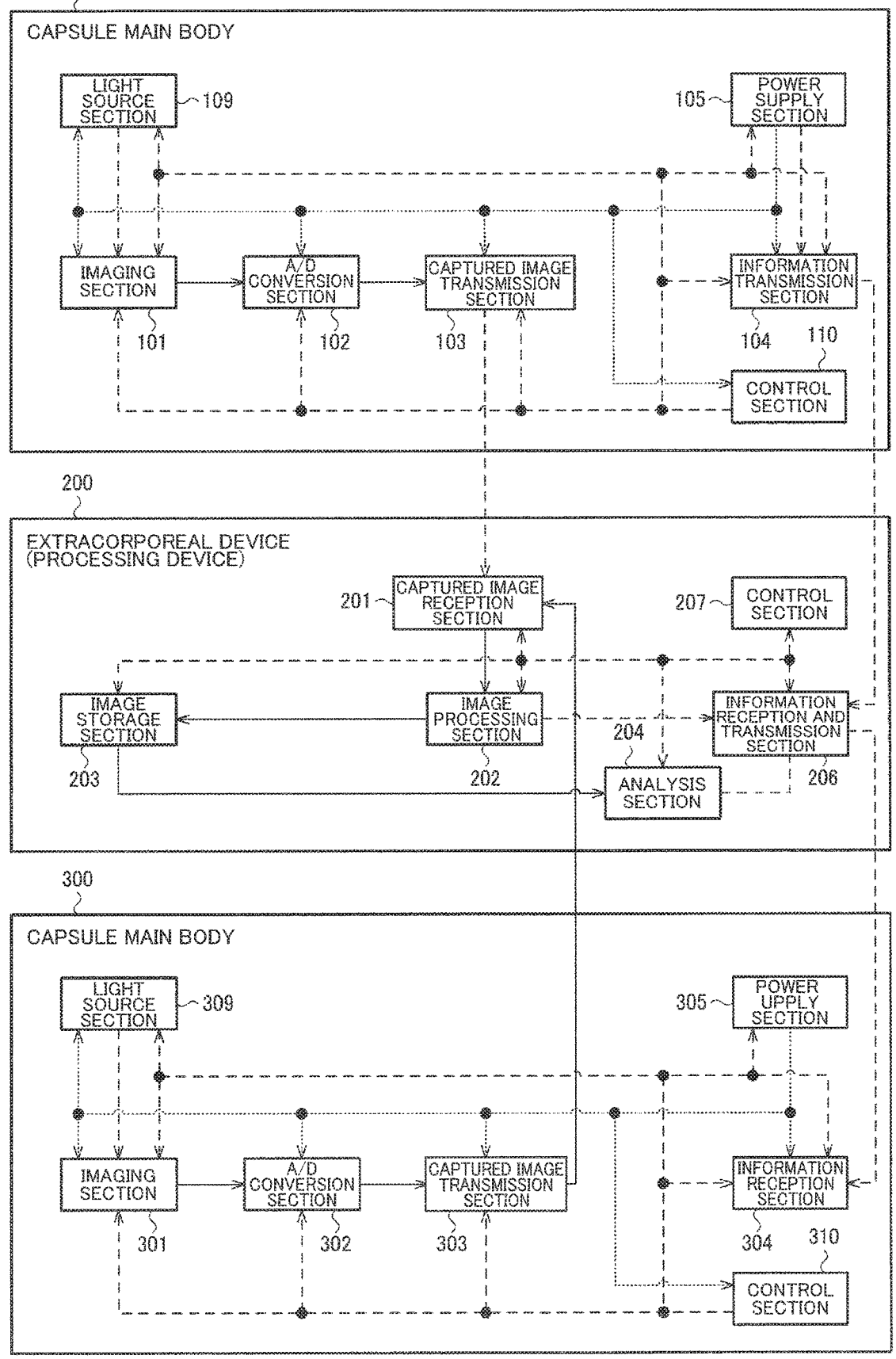
FIG. 3 illustrates an example of a configuration of an endoscope system according to a second embodiment.

FIG. 3 illustrates an example of a configuration of an endoscope system according to a second embodiment. The endoscope system includes the first capsule endoscope device 100, the extracorporeal device 200 (in a wide sense, processing device), and the second capsule endoscope device 300. The first capsule endoscope device 100 includes an imaging section 101, an A/D conversion section 102, the captured image transmission section 103, the information transmission section 104, a power supply section 105, a light source section 109, and the control section 110 (first controller). The extracorporeal device 200 includes a captured image reception section 201, an image processing section 202, an image storage section 203 (memory), an analysis section 204, an information reception and transmission section 206, and a control section 207. The second capsule endoscope device 300 includes an imaging section 301, an A/D conversion section 302, the captured image transmission section 303, the information reception section 304, a power supply section 305, a light source section 309, and the control section 310 (second controller).

In the first capsule endoscope device 100, the light source section 109 irradiates an object with illumination light, based on control performed by the control section 110. Reflected light from the object is made incident on an image sensor of the imaging section 101 via an optical lens system of the imaging section 101. The image sensor of the imaging section 101 transfers an analog captured image to the A/D conversion section 102. For example, the image sensor corresponds to a primary color single panel array (Bayer array) image sensor.

The imaging section 101 is connected to the captured image transmission section 103 via the A/D conversion section 102. The captured image transmission section 103 is wirelessly connected to the captured image reception section 201 in the extracorporeal device 200. The information transmission section 104 is wirelessly connected to the information reception and transmission section 206 in the extracorporeal device 200. The light source section 109 is connected to the imaging section 101, the A/D conversion section 102, the captured image transmission section 103, the information transmission section 104, the light source section 109, and the control section 110. The control section 110 is bidirectionally connected to the imaging section 101, the A/D conversion section 102, the captured image transmission section 103, the information transmission section 104, the power supply section 105, and the light source section 109.

The A/D conversion section 102 converts the analog captured image from the imaging section 101 into a digital captured image (hereinafter, abbreviated as a captured image), based on control performed by the control section 110, and transfers the resultant captured image to the captured image transmission section 103. The captured image transmission section 103 wirelessly transmits the captured image to the captured image reception section 201 in the extracorporeal device 200, under control by the control section 110.

In the present embodiment, the captured image is not compressed to be wirelessly transmitted to the extracorporeal device 200. However, this configuration should not be construed in a limiting sense. For example, the captured image may be compressed and then transmitted to the extracorporeal device 200.

The power supply section 105 constantly supplies power to the sections of the first capsule endoscope device 100. When the amount of power stored in the power supply section 105 (remaining battery charge) drops to or below the predetermined amount, a signal, serving as information indicating that the power almost turns OFF (for example, the power turns OFF in 15 minutes), is wirelessly transmitted to the information reception and transmission section 206 in the extracorporeal device 200, via the information transmission section 104.

In the extracorporeal device 200, the captured image reception section 201 is connected to the image storage section 203 via the image processing section 202. The information reception and transmission section 206 is wirelessly connected to the information reception section 304 in the second capsule endoscope device 300. The image storage section 203 is connected to the information reception and transmission section 206 via the analysis section 204. The control section 207 is bidirectionally connected to the captured image reception section 201, the image processing section 202, the image storage section 203, the analysis section 204, and the information reception and transmission section 206.

The captured image reception section 201 receives a captured image wirelessly transferred from the first capsule endoscope device 100, and transfers the captured image to the image processing section 202.

The image processing section 202 performs image processing on the captured image from the captured image reception section 201, based on control performed by the control section 207. For example, known interpolation processing, color management processing, edge enhancement processing, grayscale transformation processing, and the like are performed. The image processing section 202 transfers a three-plate RGB image (image including pixels each having pixel values RGB), obtained by the processing, to the image storage section 203, based on control performed by the control section 207. The image storage section 203 stores the RGB image as an image captured by the first capsule endoscope device 100.

The present embodiment is directed to an endoscope in a capsule form that captures images, while passing through the small intestine and the large intestine, to be used for diagnosis for lesion based on the captured image. To reduce the risk of insufficient diagnosis due to the battery of the endoscope in the capsule form running out before the capsule is excreted from the living body, two endoscopes in the capsule form are introduced into the patient's body at different timings. The first capsule endoscope device 100 is first swallowed by the patient. Then, the second capsule endoscope device 300 is swallowed by the patient after a predetermined period of time (for example, few hours, several tens of hours, or few days). The feature of the present embodiment is that the two endoscopes in the capsule form continuously capture images in the patient's body by the relay system.

The first capsule endoscope device 100 continuously captures images after being introduced into the patient's body and wirelessly transmits the captured images to the captured image reception section 201 in the extracorporeal device 200 via the captured image transmission section 103. When the predetermined period of time elapses after the first capsule endoscope device 100 has been introduced, the second capsule endoscope device 300 is introduced into the patient's body. The second capsule endoscope device 300 is set to be in a sleep mode, and does not start capturing images immediately after being introduced into the patient's body. In the sleep mode, no image is captured so that the power consumption is reduced. In the sleep mode, the information reception section 304 waits for the signal information (trigger signal) for starting the image capturing, from the information reception and transmission section 206 in the extracorporeal device 200. Alternatively, the second capsule endoscope device 300 may start capturing image at a low imaging frame rate (for example, 6 fpm: six images per minute) after being introduced into the patient's body. The frame rate may be switched to a high imaging frame rate when the signal information (trigger signal) for starting the image capturing is received from the information reception and transmission section 206 in the extracorporeal device 200. How the signal information, for causing the second capsule endoscope device 300 to start capturing images, is transmitted from the information reception and transmission section 206 is described later.

When the signal information for starting the imaging is transmitted from the information reception and transmission section 206 to the information reception section 304, the imaging section 301 is operated to start capturing images based on control performed by the control section 310. The analog captured image output from the image sensor of the imaging section 301 is transferred to the A/D conversion section 302. The A/D conversion section 302 converts the analog captured image from the imaging section 301 into a digital captured image (hereinafter, abbreviated as a captured image), and transfers the resultant captured image to the captured image transmission section 303, based on control performed by the control section 310. The captured image transmission section 303 wirelessly transmits the captured image to the captured image reception section 201 in the extracorporeal device 200, based on control performed by the control section 310.

In the present embodiment, the captured image is not compressed to be wirelessly transmitted to the extracorporeal device 200. However, this configuration should not be construed in a limiting sense. For example, the captured image may be compressed and then transmitted to the extracorporeal device 200.

The image processing section 202 performs image processing on the captured image from the captured image reception section 201, based on control performed by the control section 207. For example, known interpolation processing, color management processing, edge enhancement processing, grayscale transformation processing, and the like are performed. The image processing section 202 transfers a three-plate RGB image, obtained by the processing, to the image storage section 203, based on control performed by the control section 207. The image storage section 203 stores the RGB image as an image captured by the second capsule endoscope device 300.

For example, the light source sections 109 and 309 each include: a light source such as an LED; and a lens through which illumination light from the light source is emitted onto an object. For example, the imaging sections 101 and 301 each include an objective lens and an image sensor that photoelectrically converts an image formed with the objective lens. For example, the A/D conversion section 102 includes an A/D conversion circuit embedded in a chip, a CPU, or the like of the image sensor, or an A/D conversion circuit formed as an ASIC or the like. For example, the power supply sections 105 and 305 each include a battery and a power supply circuit that supplies power from the battery to each section. For example, the captured image transmission sections 103 and 303, the information transmission section 104, the information reception section 304, the captured image reception section 201, and the information reception and transmission section 206 each include a wireless communication circuit formed as an ASIC or the like or a wireless communication circuit embedded in the CPU or the like. For example, the control sections 110, 207 and 310, the image processing section 202, and the analysis section 204 each include a processing device formed as a CPU, an MPU, an ASIC, or the like. For example, the image storage section 203 includes a storage device such as a RAM, a non-volatile memory, a hard disk drive, or an optical drive.

For example, the extracorporeal device 200 may be a processing device designed as a dedicated component of an endoscope system. Alternatively, a general-purpose processing device (such as a personal computer, a server, or a mobile device for example) may be used as the extracorporeal device. In such a case, the functions of the extracorporeal device may be implemented as application software.

2.2. Operation of Endoscope System

How the signal information (trigger information), for causing the second capsule endoscope device 300 to start capturing images, is transmitted to the second capsule endoscope device 300 is described below.

Figure 4:
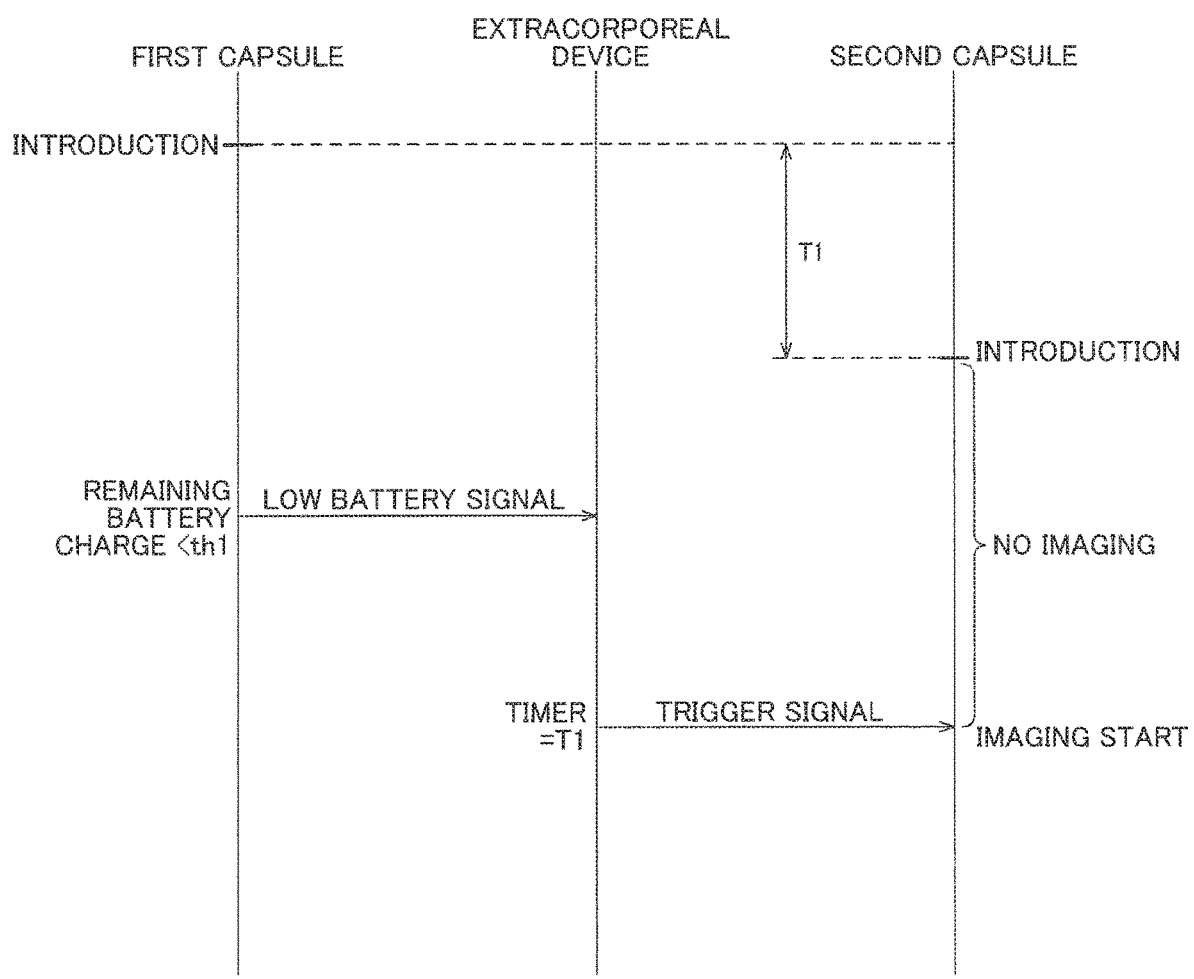
FIG. 4 illustrates a first operation example.

FIG. 4 illustrates a first operation example. When the remaining amount of power (remaining battery charge) in the power supply section 105 drops to or below a predetermined amount th1 after the first capsule endoscope device 100 has been introduced into the living body, the signal information (low battery signal) indicating that the power almost turns OFF is wirelessly transmitted to the information reception and transmission section 206 in the extracorporeal device 200 via the information transmission section 104.

When the information reception and transmission section 206 receives the low battery signal from the first capsule endoscope device 100, the control section 207 measures time elapsed after the timing at which the low battery signal has been received with a timer. When the control section 207 detects that the timer count has reached a time period T1 between the introduction of the first capsule endoscope device 100 and the introduction of the second capsule endoscope device 300, the information reception and transmission section 206 transmits the trigger signal to the information reception section 304 of the second capsule endoscope device 300. When the information reception section 304 receives the trigger signal, the control section 310 causes the imaging section 301 to start capturing images. For example, before the trigger signal is received, no power is supplied from the power supply section 305 to the light source section 309, the imaging section 301, the A/D conversion section 302, or the captured image transmission section 303. Thus, the information reception section 304 and the control section 310 are in a state of waiting for the trigger signal. When the trigger signal is received, the power supply section 305 starts supplying power to the sections, and thus the image capturing starts. In this manner, the power is saved in the second capsule endoscope device 300 until the imaging operation is started by the trigger signal.

Alternatively, the imaging section 301 may perform imaging at a frame rate lower than a normal frame rate before the information reception section 304 receives the trigger signal. In this configuration, the power supply section 305 supplies power to the sections in a power saving manner, with frequencies of light emission by the light source section 309, imaging by the imaging section 301, and transmission of images by the captured image transmission section 303 set to be lower as in the case of the frame rate.

The time to be measured by the timer needs not to be the same as the difference T1 between the introduction timings. For example, time shorter (or longer) than the difference T1 between the introduction timings by predetermined time a may be measured, and the trigger signal may be transmitted when the measured time elapses. When the first capsule endoscope device 100 and the second capsule endoscope device 300 move at the same speed in the living body, the second capsule endoscope device 300 may be started after the time T1. Actually, the devices move at different speeds, and thus the measured time may be set based on the difference in the speed.

In the description above, the first capsule endoscope device 100 transmits the low battery signal to the extracorporeal device 200. However, this should not be construed in a limiting sense, and the first capsule endoscope device 100 may directly transmit the low battery signal to the second capsule endoscope device 300 (not via the extracorporeal device 200). For example, the second capsule endoscope device 300 starts capturing images immediately after the low battery signal is received (or with the frame rate switched to a high frame rate). Alternatively, the second capsule endoscope device 300 may generate the trigger signal, to start image capturing (or switch to the high frame rate), when predetermined time (T1 or T1±α) elapses after the low battery signal has been received.

Figure 5:
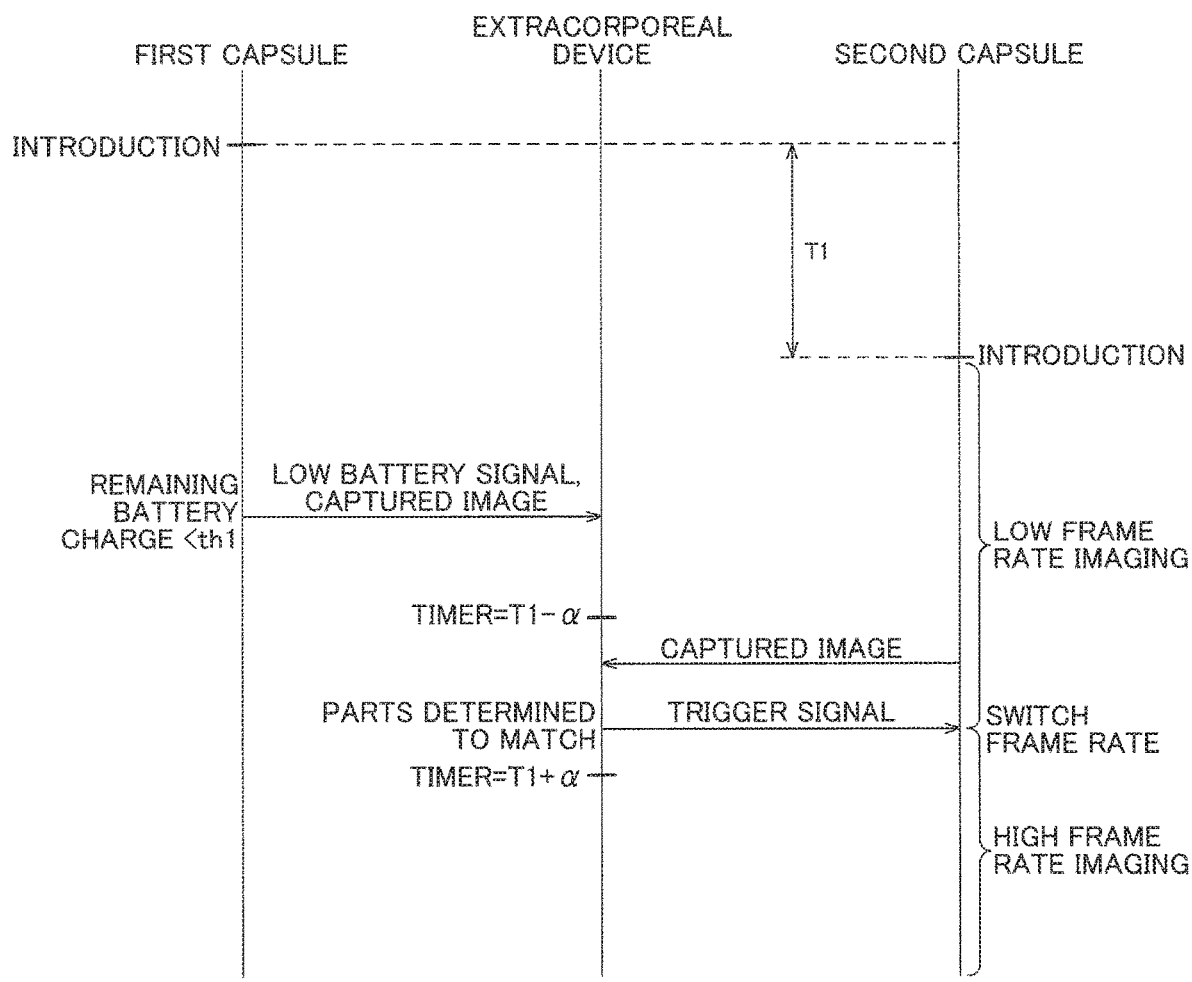
FIG. 5 illustrates a second operation example.

FIG. 5 illustrates a second operation example. In this operation example, the position of the first capsule endoscope device 100 is identified when the remaining battery charge drops to or below the predetermined amount through image recognition, whereby the risk of insufficient diagnosis is reduced with the position where the frame rate of the second capsule endoscope device 300 is switched more accurately set.

As in the first operation example, the time period between the introduction of the first capsule endoscope device 100 and the introduction of the second capsule endoscope device 300 is denoted with T1. When the remaining amount of power in the power supply section 105 (remaining battery charge) drops to or below the predetermined amount th1, the low battery signal is wirelessly transmitted to the information reception and transmission section 206 in the extracorporeal device 200 via the information transmission section 104.

In the second operation example, the imaging section 301 performs imaging at a low imaging frame rate (for example, 6 fpm: six images per minute) after the second capsule endoscope device 300 has been introduced into the living body. The captured image transmission section 303 transmits the images thus captured to the captured image reception section 201 in the extracorporeal device 200. The imaging section 101 of the first capsule endoscope device 100 performs imaging at a normal frame rate (for example, 6 fps: six images per second). The captured image transmission section 103 transmits the images thus captured to the captured image reception section 201 in the extracorporeal device 200.

When the low battery signal is received, the image storage section 203 transfers images, captured before and after the received timing, to the analysis section 204. For example, the transferred captured images include images captured between a timing that earlier by a predetermined time period than the reception of the low battery signal and a timing at which the position is determined to have matched after the reception of the low battery signal. The images captured by both the first and the second capsule endoscope devices 100 and 300 are transferred as the captured images.

The analysis section 204 analyzes the position of the first capsule endoscope device 100 in the living body at the timing of reception of the low battery signal by the extracorporeal device 200, based on the images captured by the first capsule endoscope device 100, through image processing, and also analyzes the position of the second capsule endoscope device 300 in the living body, based on the images captured by the second capsule endoscope device 300, through image processing. When the analysis section 204 determines that the position of the second capsule endoscope device 300 matches the position of the first capsule endoscope device 100 at the timing of the reception of the low battery signal by the extracorporeal device 200, the information reception and transmission section 206 transmits the trigger signal to the second capsule endoscope device 300.

When the information reception section 304 receives the trigger signal, the control section 310 switches the imaging frame rate of the imaging section 301 from the low imaging frame rate to the high imaging frame rate (for example, 6 fps: six images per second). Alternatively, after the trigger signal has been received, a movement amount (for example, a motion vector) of an object may be detected from the captured image, and the imaging frame rate may be switched among various stages (for example, 2 fps to 12 fps) in accordance with the movement amount. A higher imaging frame rate is set for a larger movement amount to prevent insufficient imaging.

2.3. Analysis Section

Figure 6:
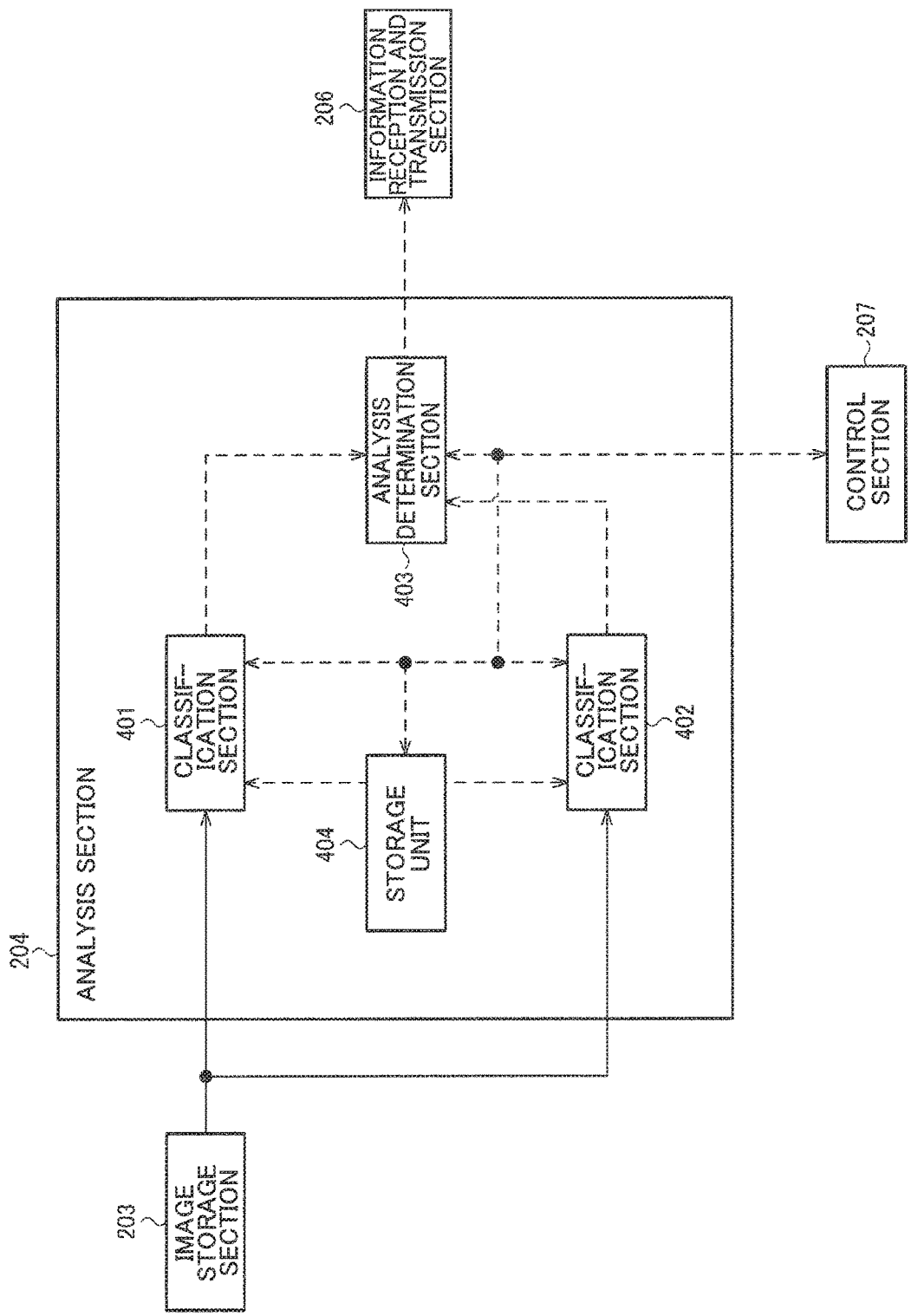
FIG. 6 illustrates an example of a configuration of an analysis section in detail.

FIG. 6 illustrates an example of a configuration of the analysis section 204 in detail. The analysis section 204 includes a classification section 401, a classification section 402, an analysis determination section 403, and a storage section 404. The image storage section 203 is connected to each of the classification section 401 and the classification section 402. The classification section 401 and the classification section 402 are each connected to the information reception and transmission section 206 via the analysis determination section 403. The storage section 404 is connected to each of the classification section 401 and the classification section 402. The control section 207 is bidirectionally connected to the classification section 401, the classification section 402, the analysis determination section 403, and the storage section 404.

The capsule endoscope devices 100 and 300 swallowed by the patient pass through the esophagus, the stomach, the small intestine, and the large intestine in this order, to be excreted from the anus. The small intestine includes the duodenum, the jejunum, and the ileum. The stomach is connected to the jejunum via the duodenum. The ileum is connected to the large intestine via the ileocecal valve. The large intestine includes the colon and the rectum. The esophagus, the stomach, the small intestine, and the large intestine, through which the capsule endoscope devices 100 and 300 pass, all have a luminal form, but are different from each other in the color of the inner wall, distribution of the blood vessels, whether or not villi exist, the thickness of the villi, and the density of the villi distribution. In the present embodiment, the captured images are learned and classified, based on a feature quantity of at least one of color, gradient, and texture by using an image recognition technique (for example, a known image recognition technique). In the classification process, which of the parts is in the captured image is determined.

The image recognition according to the present embodiment is performed with a learning process performed and the learning result stored in the storage section 404 before the capsule endoscope devices 100 and 300 are swallowed by the patient. When the information reception and transmission section 206 receives the low battery signal from the first capsule endoscope device 100, the control section 207 performs control in such a manner that the classification section 401 reads a plurality of images captured by the first capsule endoscope device 100 (a plurality of captured images that have been captured before and after the reception of the low battery signal and subjected to the image processing) from the image storage section 203 in a time-series manner, and performs the classification process. The classification process may be performed for images captured after the reception of the low battery signal and before the battery of the power supply section 105 of the first capsule endoscope device 100 expires. The classification section 402 reads a plurality of images captured by the second capsule endoscope device 300 (a plurality of captured images that have been captured at a low frame rate before and after the reception of the low battery signal and subjected to the image processing) from the image storage section 203 in a time-series manner, and performs the classification process.

Figure 7:
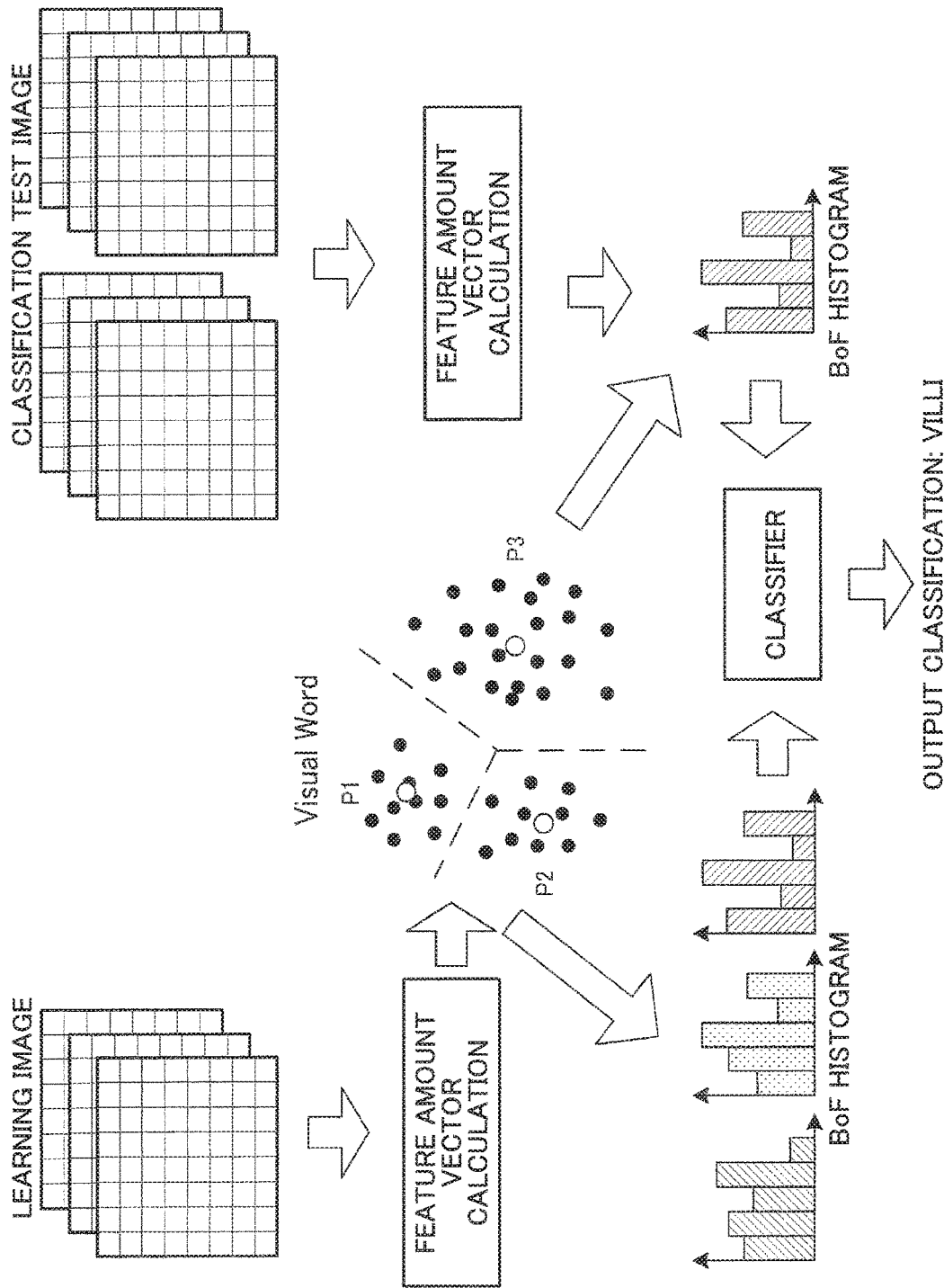
FIG. 7 illustrates a flow of a BoF algorithm process.

In the present embodiment, what is known as Bag-of-Features (BoF), an algorithm of an image recognition technique not dependent on the position of a target object, is used. FIG. 7 illustrates a flow of a BoF algorithm process. This technique is an image recognition version of Bag-of-Words that is a document search method, and is a two-stage process including learning and classifying.

In the learning stage, first of all, a plurality of learning images are selected. In the present embodiment, a plurality of villus class classification items such as "villus A", "villus B", "villus C", and the like are set based on information on the density, color, and thickness of villi. Furthermore, a plurality of mucous membrane class classification items such as "mucous membrane A", "mucous membrane B", "mucous membrane C", and the like are set based on information on the color, vascularity, and blood vessel thickness of the mucous membrane. Anything other than villi or the mucous membrane is set to be in a classification item "others". Then, a learning image including objects corresponding to these classification items is selected. The classification items may be set based on a processing cost, a classification accuracy, and the like.

In the learning, a plurality of small sample areas are extracted from the learning image. Then, a feature quantity vector is calculated through a feature quantity extraction process, and then an observation reference known as Visual Word (hereinafter, abbreviated as VW) is selected through a clustering process. For example, a known K-means method may be used. Next, the feature quantity vector is calculated for each of the small areas sequentially extracted from each learning image in a spatial direction, in a manner similar to that described above, and a distance between the feature quantity vector and the VW is obtained. The VW with the smallest distance obtains a single vote. When the vote process is completed for all the small areas in a single learning image, a BoF histogram corresponding to the image is generated. Thus, the BoF histograms in the same number as the learning images are generated. A learning classifier for classifying the images is generated, by using the BoF histograms and BoF vectors using the BoF histograms as components. For example, a learning classifier algorithm known as Support Vector Machine (SVM) may be employed.

Information on the learning classifier and information on the BoF histograms obtained from the learning image and the BoF vector using the BoF histograms as components are calculated and stored in the storage section 404 in advance.

In the classifying stage, the captured images to be classified are sequentially input. Then, the feature quantity vector is calculated for each of the small areas sequentially extracted from the captured images in the spatial direction, and the distance between the feature quantity vector and the VW is obtained as described above. The VW with the smallest distance obtains a single vote. When the voting process is completed for all the small areas in a single captured image, the BoF histogram corresponding to the captured image is generated. Then, the SVM classifier performs classification using the BoF histograms generated from the learning image, and outputs a result of the classification (classification result).

The BoF histogram is generated by using the captured image as described above. Then, the BoF histogram of the learning image stored in the storage section 404 and the BoF vector using the BoF histograms as components are compared with the BoF histogram of an image for classification from the SVM classifier and the BoF vector using the BoF histograms as components. Then, a classification index indicating a belonging classification item is provided. In this manner, the classification section 401 and the classification section 402 each classifies the read captured image and provide a classification index. The classification indices of both captured images are transferred to the analysis determination section 403.

In the configuration according to the present embodiment, the feature quantity vector is calculated with at least one of the feature quantities of color, gradient, and texture of the captured image.

Figure 8:
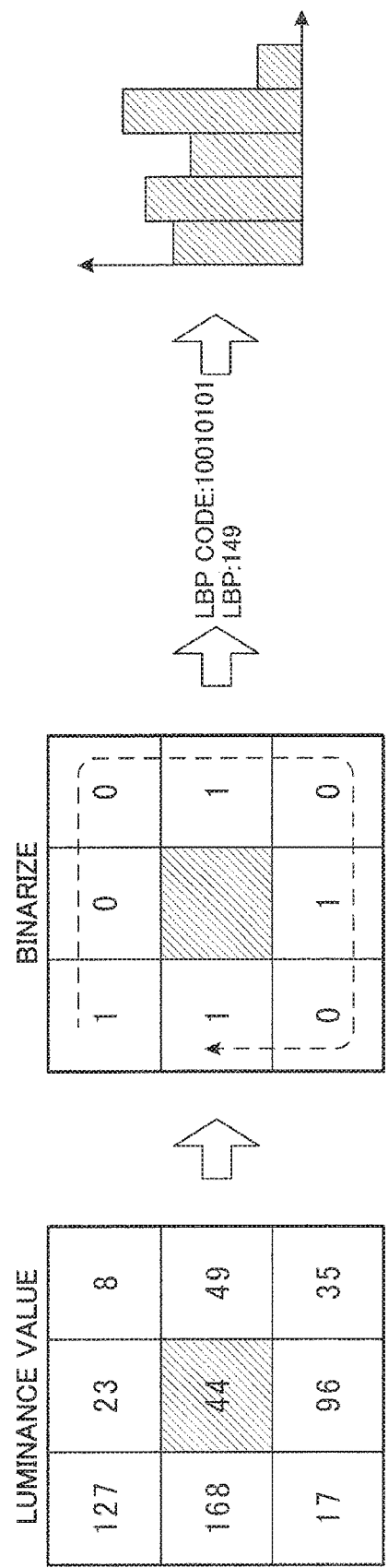
FIG. 8 illustrates a process for calculating an LBP feature quantity vector.

FIG. 8 illustrates a process for calculating a Local-Binary-Pattern (LBP) feature quantity vector. First of all, an image is segmented into blocks. In each block, cells (three pixels× three pixels) with the pixel of interest at the center are set. In the cells, 0 or 1 is allocated, based on the difference between the pixel of interest (a hatched pixel in FIG. 8) and neighboring pixels (surrounding eight pixels) in the luminance value. Then, 0 and 1 are arranged in order to generate an 8-bit LBP code. The LBP codes of all the cells in the block are integrated to generate a histogram, whereby a histogram is generated for one block. Then, a similar process is performed on the next block. In this manner, the histograms in the same number as the blocks in a single image are generated. The histogram is normalized for each block, whereby an LBP feature quantity vector is generated.

Figure 9:
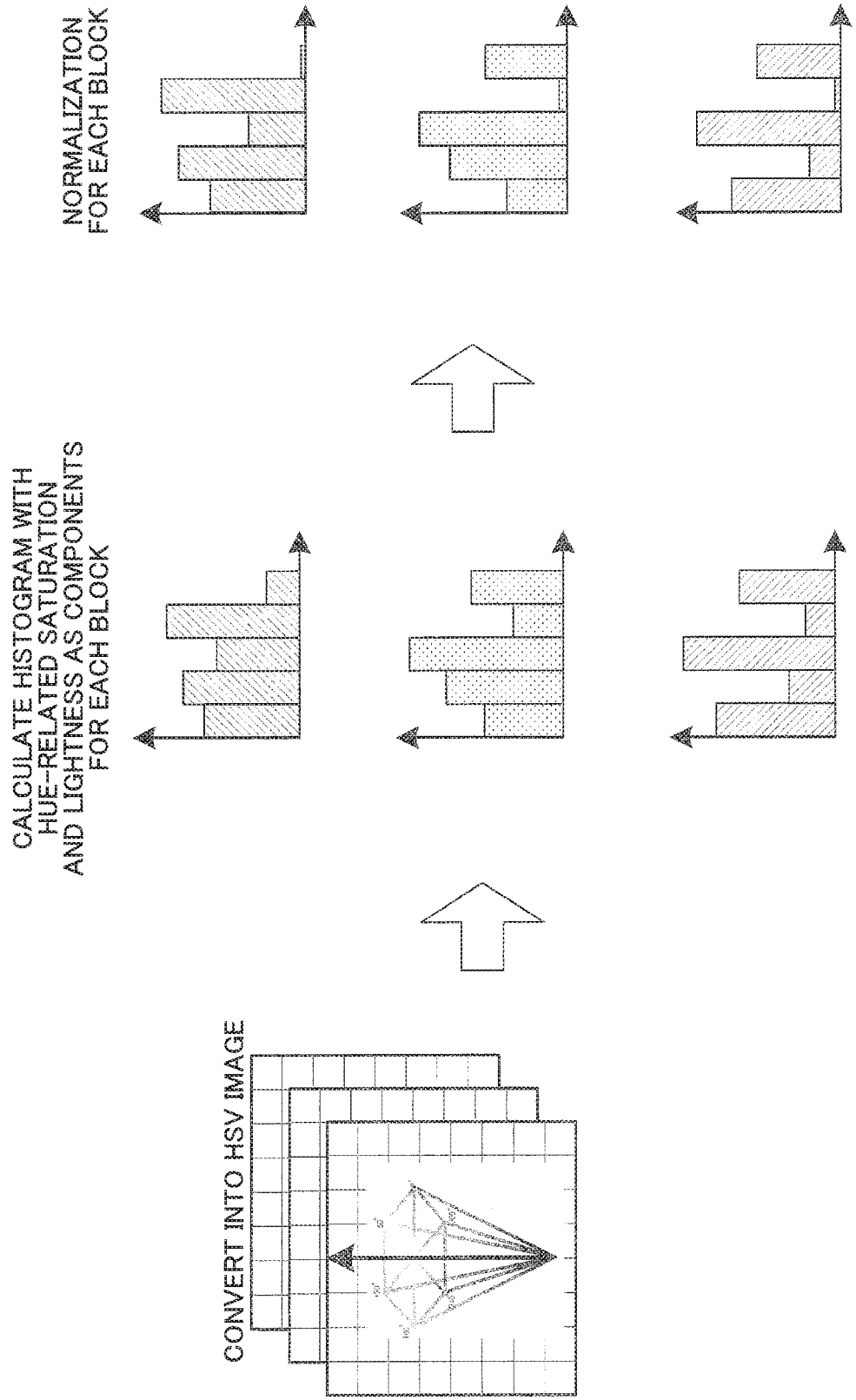
FIG. 9 illustrates a process for calculating an HSV feature quantity vector.

FIG. 9 illustrates a process for calculating a Hue-Saturation-Value (HSV: a color space including three components of Hue, Saturation, and Value (lightness)) feature quantity vector. The HSV color space is segmented into a plurality of areas in a hue direction, a saturation direction, and a lightness direction. First of all, the RGB pixel values of each pixel in the image are converted into an HSV color based pixel value. The HSV image after the conversion is segmented into blocks, and a histogram with hue-related saturation and lightness as components is calculated for one block. Then, a similar process is performed on the next block. In this manner, the histograms in the same number as the blocks in a single image are generated. Then, the histogram is normalized for each block, whereby an HSV feature quantity vector is generated.

Figure 10:
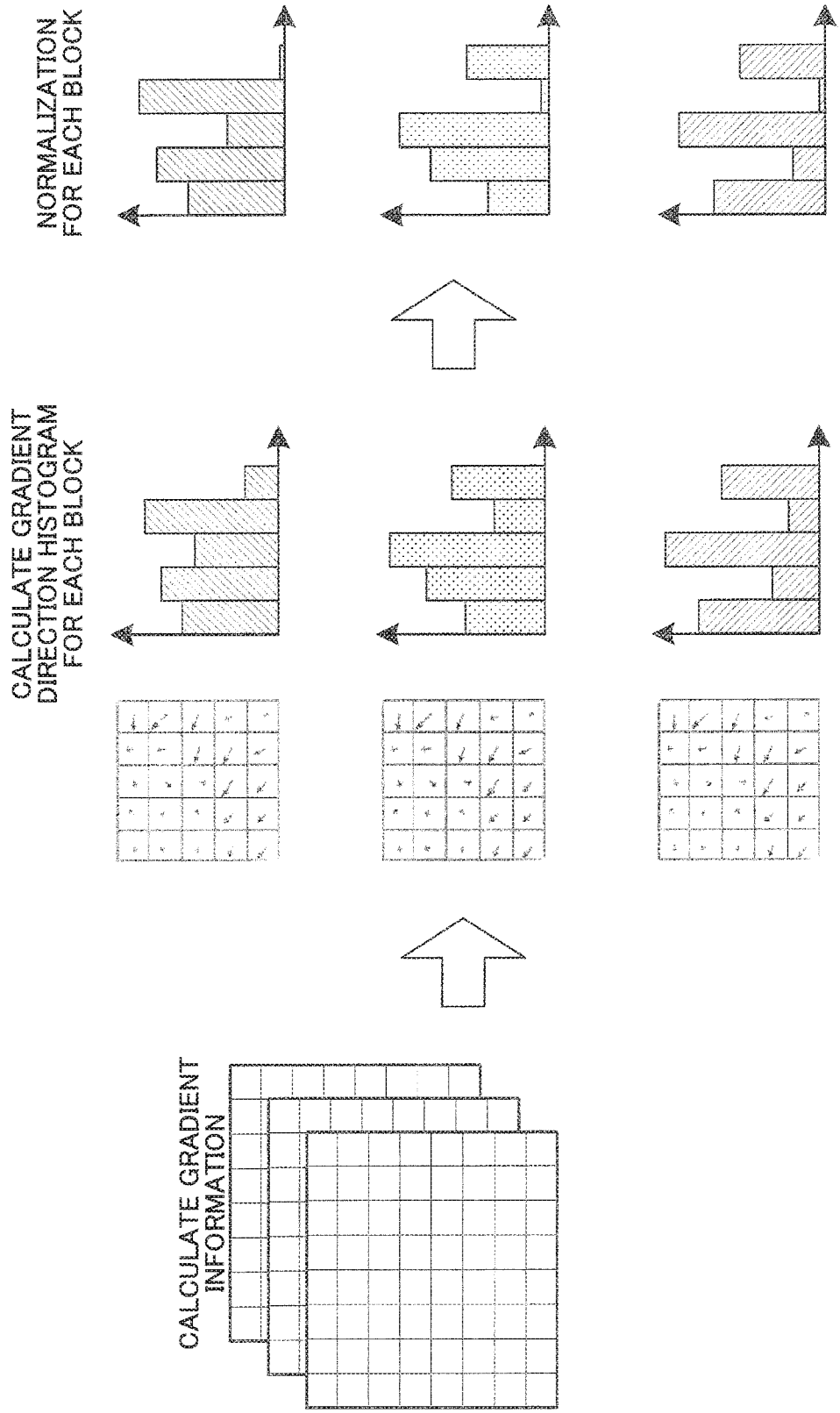
FIG. 10 illustrates a process for calculating an HOG feature quantity vector.

FIG. 10 illustrates a process for calculating a Histogram-of-Oriented-Gradient (HOG) feature quantity vector. A local area of the image is segmented into blocks. Luminance gradient information (gradient direction, weight, and the like) is calculated for each pixel, and a histogram of the luminance gradient is calculated for one block. Then, a similar process is performed on the next block. In this manner, the histograms in the same number as the blocks in a single image are generated. Then, the histogram is normalized for each block, whereby an HOG feature quantity vector is generated.

The configuration according to the embodiment described above performs learning and classifying by using the LBP feature quantity, the HSV feature quantity, and the HOG feature quantity. However, this configuration should not be construed in a limiting sense. The learning and classifying may be executed by using any appropriate feature quantity, related to gradient, color, and texture.

Figure 11:
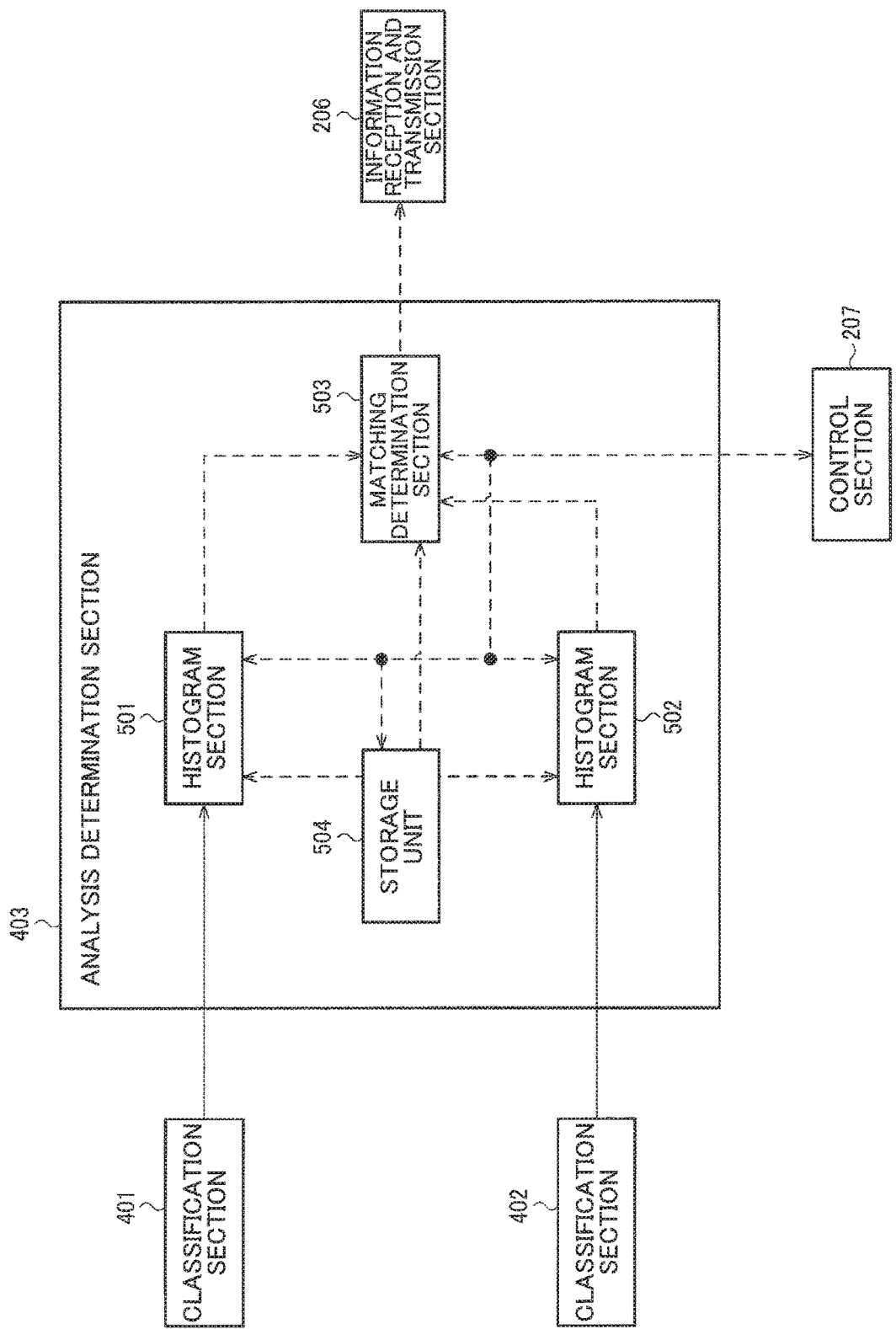
FIG. 11 illustrates an example of a configuration of an analysis determination section in detail.

FIG. 11 illustrates an example of a configuration of the analysis determination section 403 in detail. The analysis determination section 403 includes a histogram section 501, a histogram section 502, a matching determination section 503, and a storage section 504. The classification section 401 is connected to the histogram section 501. The classification section 402 is connected to the histogram section 502. The histogram section 501 and the histogram section 502 are each connected to the matching determination section 503. The storage section 504 is connected to each of the histogram section 501, the histogram section 502, and the matching determination section 503. The control section 207 is bidirectionally connected to the histogram section 501, the histogram section 502, the matching determination section 503, and the storage section 504.

The histogram section 501 uses a result of classifying the captured images from the classification section 401 to generate a histogram based on the classification item, and transfers the resultant histogram to the matching determination section 503. Specifically, the histogram is generated by counting the number of captured images classified into each of the villi A to C, the mucous membranes A to C, and other classification items. Similarly, the histogram section 502 uses a result of classifying the captured image from the classification section 402 to generate a histogram based on the classification item, and transfers the resultant histogram to the matching determination section 503.

Before the trigger signal is received, the second capsule endoscope device 300 captures images at a low imaging frame rate, and the first capsule endoscope device 100 captures images at a high imaging frame rate higher than the low imaging frame rate. This means that the devices capture different number of images in the same period. Thus, the analysis section 204 performs thinning process on the images captured by the first capsule endoscope device 100. For example, when the imaging frame rate of the first capsule endoscope device 100 is 6 fpm whereas the imaging frame rate of the second capsule endoscope device 300 is 2 fpm, one of every three images captured in time series by the first capsule endoscope device 100 is extracted. Thus, the same number of captured images can be compared in a unit time.

Figure 12:
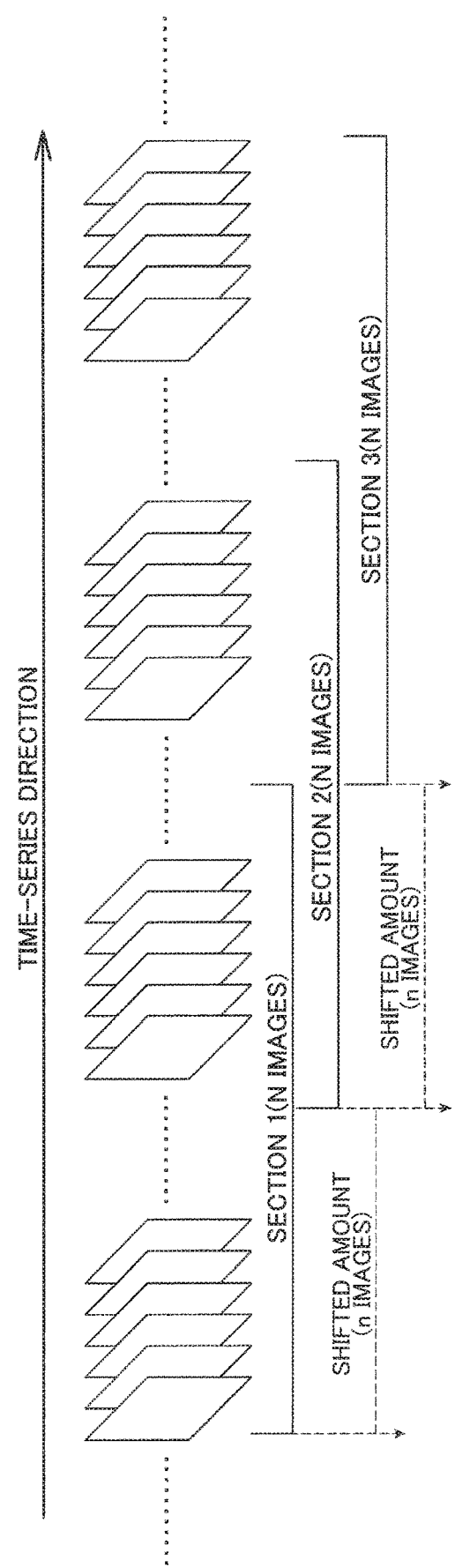
FIG. 12 illustrates a histogram generation process.

FIG. 12 illustrates a histogram generation process. A period (for example, 15 minutes) between the transmission of the low battery signal from the first capsule endoscope device 100 to the extracorporeal device 200 and the power down is denoted with P1. The histogram section 501 generates the histogram based on the result of classifying images (the number of images is denoted with N) after the thinning of the images captured by the first capsule endoscope device 100, in the period P1, based on control performed by the control section 207. The histogram thus generated is transferred to the matching determination section 503. The histogram section 502 generates a histogram based on a classification result within a single comparison section, and transfers the histogram to the matching determination section 503, based on control performed by the control section 207. One comparison section includes N images captured in time series by the second capsule endoscope device 300 after receiving the trigger signal. After the histogram of a single section has been generated, the same determination is performed for another section including the next N images, shifted from the previous section by n images (n being an integer satisfying n≥1) in the time series direction. In this manner, the histogram based on the classification result is repeatedly generated for each section, and transferred to the matching determination section 503.

Figure 13:
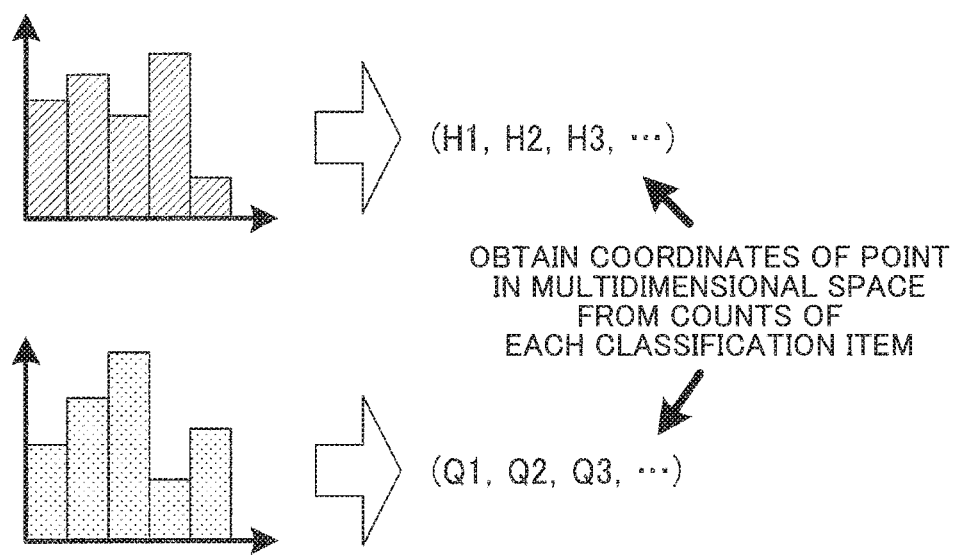
FIG. 13 illustrates a process for determining whether or not histograms match.

The matching determination section 503 compares the histogram transferred from the histogram section 501 with the histograms sequentially transferred from the histogram section 502, based on control performed by the control section 207. For example, as illustrated in FIG. 13, the comparison is performed based on the Euclidean distance between two histograms H and W, respectively generated by the histogram sections 501 and 502.

[Formula 1]

$$d(H,Q) = \sqrt{\Sigma(Hi - Qi)^2} \qquad (1)$$

The matching determination section 503 determines that the two histograms H and Q completely match, when a value of d(H,Q) calculated with Formula (1) described above is 0.

When d(H,Q) is smaller than a predetermined threshold value, the two histograms H and Q are determined to be similar to each other. Thus, the first capsule endoscope device 100 determines that the second capsule endoscope device 300 has reached a location (part) where the first capsule endoscope device 100 is located within a period between the transmission of the low battery signal and the power down. The matching determination section 503 transfers information, indicating that the location has been reached, to the information reception and transmission section 206. The information reception and transmission section 206 wirelessly transmits a signal (trigger signal) for switching the imaging frame rate to the second capsule endoscope device 300, based on control performed by the control section 207. Upon receiving the signal for switching the imaging frame rate, the information reception section 304 of the second capsule endoscope device 300 controls the imaging section 301 so that switching from the low imaging frame rate to the high imaging frame rate can be achieved.

The configuration described above uses the Euclidean distance to compare the histograms based on the classification results. However, this configuration should not be construed in a limiting sense. For example, a stereoscopic or correlation method or the like may be used for comparing histograms.

As described above, by using the image recognition technique, the images captured by the first capsule endoscope device 100 during the period between the transmission of the low battery signal and the power down are compared with images captured in time series by the second capsule endoscope device 300 after receiving the trigger signal. In this process, a single comparison section is set to include N images captured in time series. The histograms are generated based on the classification result in the section, and sequentially compared in each of the sections. Thus, the second capsule endoscope device 300 can be determined to have reached the location where the first capsule endoscope device 100 reached before the power runs out. Then, the imaging frame rate of the second capsule endoscope device 300 is switched from low to high. Thus, the images inside the patient's body can be captured by the relay system using two capsule endoscope devices. All things considered, a risk of insufficient diagnosis due to discharged battery can be reduced compared with the case where only one capsule endoscope is used.

2.4. Modification

In the description above, a location where the capsule endoscope, first introduced into the patient, has stopped due to discharged battery is identified by using an image recognition technique. However, this configuration should not be construed in a limiting sense, and the position can be identified with a field intensity for example.

Figure 14:
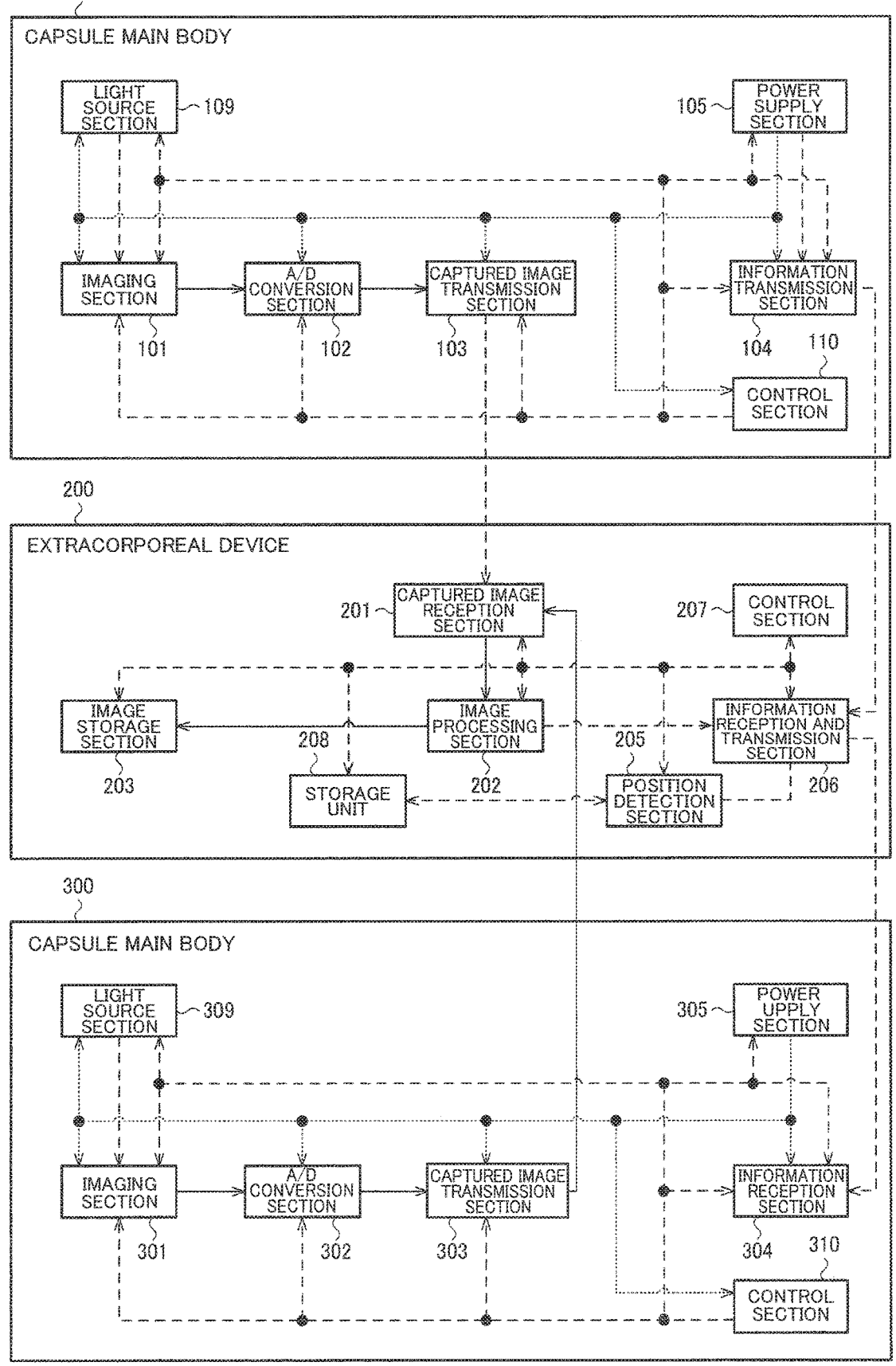
FIG. 14 illustrates an example of a configuration of an endoscope system according to a modification of the second embodiment.

FIG. 14 illustrates an example of a configuration of an endoscope system according to this modification. The endoscope system includes the first capsule endoscope device 100, the extracorporeal device 200, and the second capsule endoscope device 300. The first capsule endoscope device 100 includes the imaging section 101, the A/D conversion section 102, the captured image transmission section 103, the information transmission section 104, the power supply section 105, the light source section 109, and the control section 110. The second capsule endoscope device 300 includes the imaging section 301, the A/D conversion section 302, the captured image transmission section 303, the information reception section 304, the power supply section 305, the light source section 309, and the control section 310. The extracorporeal device 200 includes the captured image reception section 201, the image processing section 202, the image storage section 203 (memory), the position detection section 205, the information reception and transmission section 206, the control section 207, and the storage section 208 (memory). The components that have already been described are denoted with the same reference numerals, and the description thereof is omitted as appropriate.

In the extracorporeal device 200, the captured image reception section 201 is connected to the image storage section 203 via the image processing section 202. The information reception and transmission section 206 is wirelessly connected to the information reception section 304 in the second capsule endoscope device 300. The position detection section 205 is connected to the information reception and transmission section 206. The storage section 208 is bidirectionally connected with the position detection section 205. The control section 207 is bidirectionally connected with the captured image reception section 201, the image processing section 202, the image storage section 203, the position detection section 205, the information reception and transmission section 206, and the storage section 208.

For example, a plurality of reception antennae, for receiving captured images wirelessly transmitted from the capsule endoscope devices 100 and 300 to the extracorporeal device 200, are attached to the living body surface of the patient. The extracorporeal device 200 is provided with the position detection section 205.

The first capsule endoscope device 100 transmits the low battery signal to the information reception and transmission section 206 in the extracorporeal device 200 via the information transmission section 104 before the power runs out, under the control performed by the control section 110. When the information reception and transmission section 206 receives the low battery signal, the control section 207 in the extracorporeal device 200 operates the position detection section 205.

The position detection section 205 uses the plurality of antennae, attached to the patient's body surface, to detect the position of the first capsule endoscope device 100 in the patient's body, based on control performed by the control section 207. Specifically, the position of the first capsule endoscope device 100 in the patient's body is detected by three-dimensional positioning or the like for example, based on the position of each antenna attached to the patient's body surface and the field intensity of a reception signal received by the antenna. The position detection section 205 stores information of the position thus detected in the storage section 208.

In the same manner, the position detection section 205 continues to detect the position of the second capsule endoscope device 300 in the patient's body. When the position detection section 205 determines that the position of the second capsule endoscope device 300 matches the position of the first capsule endoscope device 100 stored in the storage section 208, the information reception and transmission section 206 wirelessly transmits the trigger signal to the information reception section 304 in the second capsule endoscope device 300, based on control performed by the control section 207. Upon receiving the trigger signal, the second capsule endoscope device 300 controls the imaging section 301 so that switching from the low imaging frame rate to the high imaging frame rate is achieved.

Various modifications may be employed for identifying the positions. For example, when the capsule endoscope first introduced into the patient's body transmits the low battery signal, the position of the capsule endoscope may be identified through inspection using radiation such as X-ray or CT or using ultrasonic waves. When it has been confirmed that the subsequently-introduced capsule endoscope has reached the same position, the imaging by the subsequently-introduced capsule endoscope may be controlled. For example, the extracorporeal device 200 may be provided with a button or the like, and the trigger signal may be transmitted to the second capsule endoscope device 300 when the physician presses the button.

In the embodiment described above, the two capsule endoscope devices are introduced into the patient's body at two different timings. However, this procedure should not be construed in a limiting sense. For example, the two capsule endoscope devices may be integrated (two sets of endoscope devices may be accommodated in a single capsule casing) to be introduced into the patient's body at once. A first capsule endoscope device first starts capturing images, while a second capsule endoscope device is not operated (or captures images at a low frame rate). The second capsule endoscope device starts capturing images (or captures images with the frame rate switched from low to high) before the battery of the first capsule endoscope device runs out.

In the embodiment described above, the patient's body is examined by the relay system using the two capsule endoscope devices. However, this should not be construed in a limiting sense. For example, the patient's body may be examined by a relay system using three or more capsule endoscope devices depending on the situation.

The endoscope system according to the second embodiment described above includes the processing device that outputs the trigger signal upon receiving the first information on the first capsule endoscope device 100. When the second control section 310 in the second capsule endoscope device 300 receives the trigger signal from the processing device, the second control section 310 performs the change process for the imaging operation performed by the second image sensor 320 (in the imaging section 301).

With this configuration, the processing device that has received the first information from the first capsule endoscope device 100 can generate the trigger signal based on the first information to make the second capsule endoscope device 300 start the imaging operation (or perform the imaging operation with the frame rate switched).

The processing device according to the second embodiment corresponds to the extracorporeal device 200 illustrated in FIG. 3. However, this should not be construed in a limiting sense, and the processing device may be incorporated in the second capsule endoscope device 300 as described later with reference to FIG. 17. In such a configuration, the endoscope system may not include the extracorporeal device, or may include an extracorporeal device for accumulating the captured images.

In the present embodiment, the first capsule endoscope device 100 includes a first communication section (first communication device) that transmits first information that is information on remaining battery charge of the first capsule endoscope device 100. The processing device outputs the trigger signal when a predetermined period of time elapses after the remaining battery charge drops to or below the predetermined amount.

The first communication section according to the second embodiment corresponds to the information transmission section 104 in FIG. 3. The first communication section may further include the captured image transmission section 103.

With this configuration, the first capsule endoscope device 100 can wirelessly transmit the remaining battery charge information via the first communication section, and the processing device can generate the trigger signal upon receiving the remaining battery charge information. With the trigger signal output when the predetermined period of time elapses after the remaining battery charge drops to or below the predetermined amount, the imaging can be relayed to the second capsule endoscope device 300 after the imaging by the first capsule endoscope device 100 is disabled.

The predetermined period of time according to the present embodiment corresponds to the time difference between the introduction of the first capsule endoscope device 100 into the living body and the introduction of the second capsule endoscope device 300 into the living body.

As described above, possible examples of the time difference information include information stored in the processing device by the physician and predetermined time difference information set to the processing device in advance. The predetermined period of the time, which may be equal to the time difference between the introductions, may be obtained by adding or subtracting a margin to or from the time difference between the introductions With this configuration, the trigger signal can be output when the predetermined period of time, based on the time difference between the introductions of the two capsule endoscope devices 100 and 300 from the timing where the remaining battery charge has dropped to or below the predetermined amount, elapses. Thus, the imaging operation by the second capsule endoscope device 300 can be changed when the second capsule endoscope device 300 arrives at or around the position where the imaging by the first capsule endoscope device 100 has been disabled.

The first capsule endoscope device 100 according to the present embodiment includes the first communication section that transmits the first information including the remaining battery charge information on the first capsule endoscope device 100 and the images captured by the first capsule endoscope device 100. The processing device acquires information indicating the position of the first capsule endoscope device 100 in the living body at the timing where the remaining battery charge has dropped to or below the predetermined amount, based on the images captured by the first capsule endoscope device 100. The processing device outputs the trigger signal upon determining that the position of the second capsule endoscope device 300 in the living body matches the position indicated by the position information described above, based on the images captured by the second capsule endoscope device 300.

The position information according to the second embodiment corresponds to the classification result obtained by the classification process. Specifically, the classification is based on the density of villi, the type of the mucous membrane, or the like. These aspects differ among the parts of the digestive tract and positions therein (approximate positions (for example, the villi are arranged more densely at a portion of the small intestine more on the upper side)), and thus actually serves as classification information indicating the part of the digestive tract or the position therein. The position information is not limited to this, and may be any information indicating the position in the living body. For example, information on the position identified using the three-dimensional measurement using the antennae or using the X-ray image may be employed.

It may be determined that the position matches not only when the exact match is detected, and deviation within a certain range is tolerated. For example, when the classification result is used as described above, the positions are determined to match when the density of the villi or the type of the mucous membrane is determined to be in the same classification. Thus, the position is determined to match as long as the density of the villi or the type of the mucous membrane is determined to be in the same classification. Alternatively, the position may be determined to match when the second capsule endoscope device 300 has been determined to have reached a position within a range of the movement of the first capsule endoscope device 100 after the transmission of the low battery signal and before the imaging actually stops.

With the positions of the capsule endoscope devices 100 and 300 determined based on the captured image as described above, the imaging operation of the second capsule endoscope device 300 can be changed when the second capsule endoscope device 300 is determined to have reached the position where the imaging by the first capsule endoscope device 100 has been disabled. Thus, the relay timing can be controlled so that the images can be contiguously captured.

In the present embodiment, the processing device outputs the trigger signal when the match is determined to have occurred within a predetermined range of time, based on a predetermined time period after the remaining battery charge has dropped to or below the predetermined amount.

Thus, whether or not the second capsule endoscope device 300 has reached the position where the imaging by the first capsule endoscope device 100 has been disabled can be determined, based on two types of information including: the time difference between the introduction of the capsule endoscope devices 100 and 300; and position matching determination based on captured images. Thus, the relay timing can be more accurately determined.

The processing device according to the present embodiment corresponds to the extracorporeal device 200. The second capsule endoscope device 300 includes a second communication section (second communication device) that receives the trigger signal.

The second communication section according to the second embodiment corresponds to the information reception and transmission section 206 in FIG. 3. The second communication section may further include the captured image reception section 201.

With the extracorporeal device 200 thus used as the processing device, the extracorporeal device 200 generally used for receiving and accumulating captured images in the system including the capsule endoscope device can also be used as a control device for achieving relay imaging performed with the two capsule endoscope devices 100 and 300.

The first capsule endoscope device 100 and the second capsule endoscope device 300 may be formed as dedicated devices, or may be formed to be interchangeable through mode setting. In the latter case, the following configuration is employed for example.

Specifically, a capsule endoscope device includes: an image sensor; and the control section that controls an imaging operation by the image sensor. The capsule endoscope device may be settable to be in a first operation mode and in a second operation mode. When the capsule endoscope device is set to be in the second operation mode, the control section performs a change process for control on the imaging operation by the image sensor, based on first information on a capsule endoscope device set to be in the first operation mode. The capsule endoscope device set to be in the first operation mode is a capsule endoscope device that is introduced into the living body before the capsule endoscope device set to be in the second operation mode is.

For example, the capsule endoscope devices may include a mode setting section (for example, a register, a non-volatile memory, or the like), and a mode is set in the mode setting section through wireless communications from an external device. The mode may be set before the shipping, or may be set by the user. The first operation mode is a mode of performing an operation that is the same as that performed by the first capsule endoscope device 100 described above, whereas the second operation mode is a mode of performing an operation that is the same as that performed by the second capsule endoscope device 300 described above. The endoscope system described above includes the capsule endoscope device set to be in the first operation mode and the capsule endoscope device set to be in the second operation mode. The endoscope system may further include the extracorporeal device 200.

With this configuration, the relay imaging by the two capsule endoscope devices can be implemented with the capsule endoscope device set to be in the first mode and the capsule endoscope device set to be in the second mode. The two capsule endoscope devices can be the capsule endoscope devices with the same configuration with the switchable modes, whereby the design and manufacturing process can be simplified.

The processing device (extracorporeal device 200) according to the present embodiment may have the following configuration. The processing device includes: a third memory that stores information (for example, a program and various types of data); and a third processor (a processor including hardware) that operates based on the information stored in the third memory. The third processor outputs a trigger signal upon receiving the first information on the first capsule endoscope device 100. The second processor (control section 310) of the second capsule endoscope device 300 performs a change process for the imaging operation by the second image sensor 320 upon receiving the trigger signal from the processing device.

The third processor may have the same configuration as the first and the second processors. The third memory may have the same configuration as the first and the second memories. For example, the third memory stores a computer-readable instruction. Functions of the sections of the processing device are implemented as processes when the instruction is executed by the processor. For example, the sections of the processing device include the captured image reception section 201, the image processing section 202, the analysis section 204, the information reception and transmission section 206, and the control section 207 in FIG. 3 and FIG. 15; the captured image reception section 201, the image processing section 202, the position detection section 205, the information reception and transmission section 206, and the control section 207 in FIG. 14. The instruction may be an instruction included in an instruction set that is included in a program, or may be an instruction that causes a hardware circuit included in the processor to operate.

The operation according to the present embodiment is implemented as follows, for example. The third processor acquires the first information on the first capsule endoscope device 100, and transmits the trigger signal based on the first information. The second processor (control section 310) of the second capsule endoscope device 300 performs the change process for the imaging operation by the second image sensor 320, upon receiving the trigger signal from the processing device.

The sections of the processing device according to the present embodiment may be implemented as modules for programs operating on the processor. For example, the control section 207 is implemented as a control module that causes the information reception and transmission section 206 to output the trigger signal, upon receiving the first information on the first capsule endoscope device 100. The information reception and transmission section 206 is implemented as a communication module that outputs the trigger signal when the control section 207 receives the first information on the first capsule endoscope device 100.

3. Third Embodiment

Figure 15:
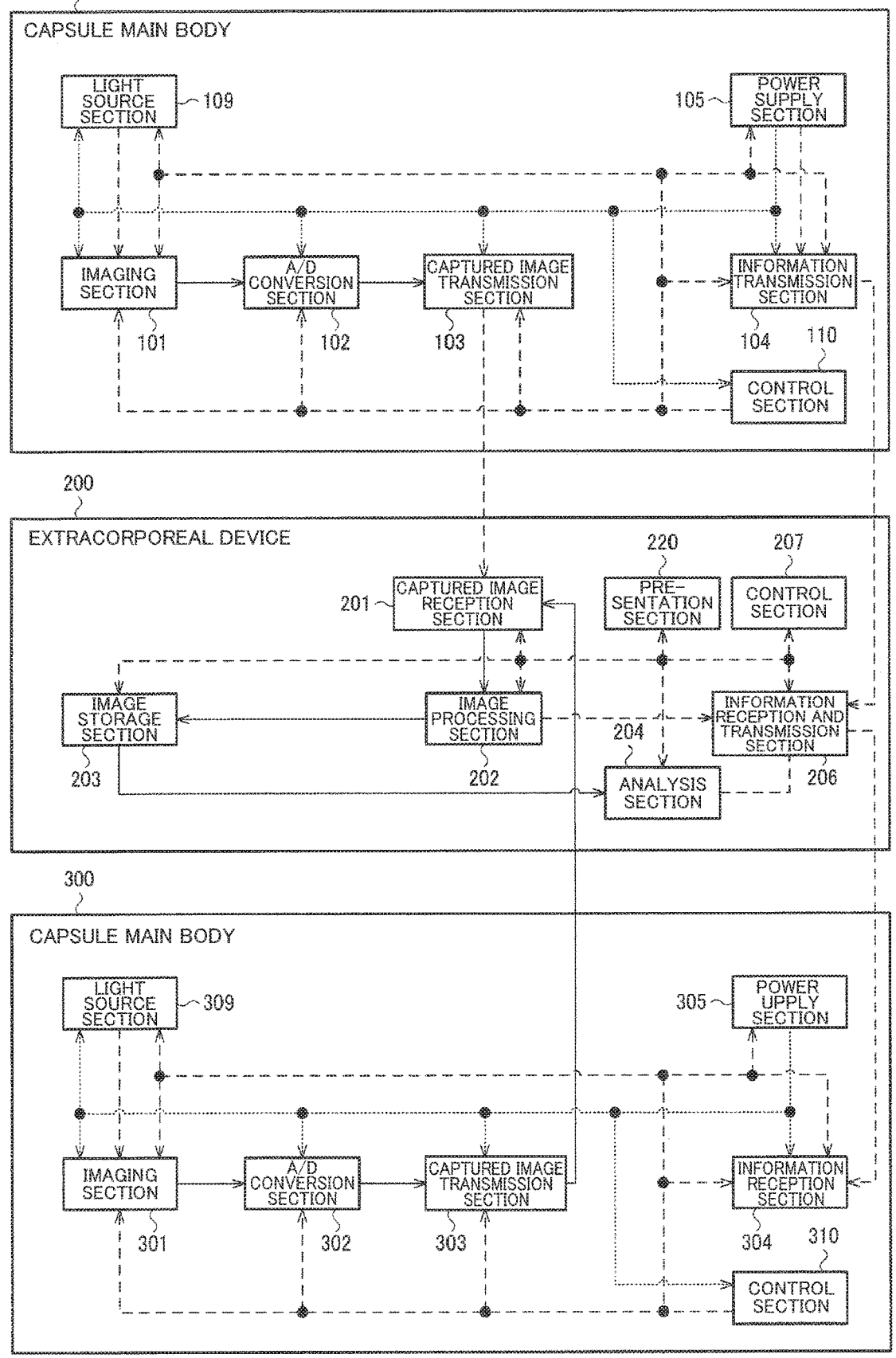
FIG. 15 illustrates an example of a configuration of an endoscope system according to a third embodiment.

FIG. 15 illustrates an example of a configuration of an endoscope system according to a third embodiment. The endoscope system includes the first capsule endoscope device 100, the extracorporeal device 200, and the second capsule endoscope device 300. The first capsule endoscope device 100 includes the imaging section 101, the A/D conversion section 102, the captured image transmission section 103, the information transmission section 104, the power supply section 105, the light source section 109, and the control section 110 (first controller). The second capsule endoscope device 300 includes the imaging section 301, the A/D conversion section 302, the captured image transmission section 303, the information reception section 304, the power supply section 305, the light source section 309, and the control section 310. The extracorporeal device 200 includes the captured image reception section 201, the image processing section 202, the image storage section 203 (memory), the analysis section 204, the information reception and transmission section 206, the control section 207 (second controller), and a presentation section 220. The components that are the same as those that have already been described are denoted with the same reference numerals, and the description thereof is omitted as appropriate.

The feature of the third embodiment lies in the timing at which the second capsule endoscope device 300 is introduced into the patient's body.

In the present embodiment, the second capsule endoscope device 300 is introduced into the patient's body when the first capsule endoscope device 100 is determined to be likely to fail to capture images of the examination target part, due to the battery of the first capsule endoscope device 100 that has been introduced into the patient's body running out before the excretion from the living body.

Figure 16:
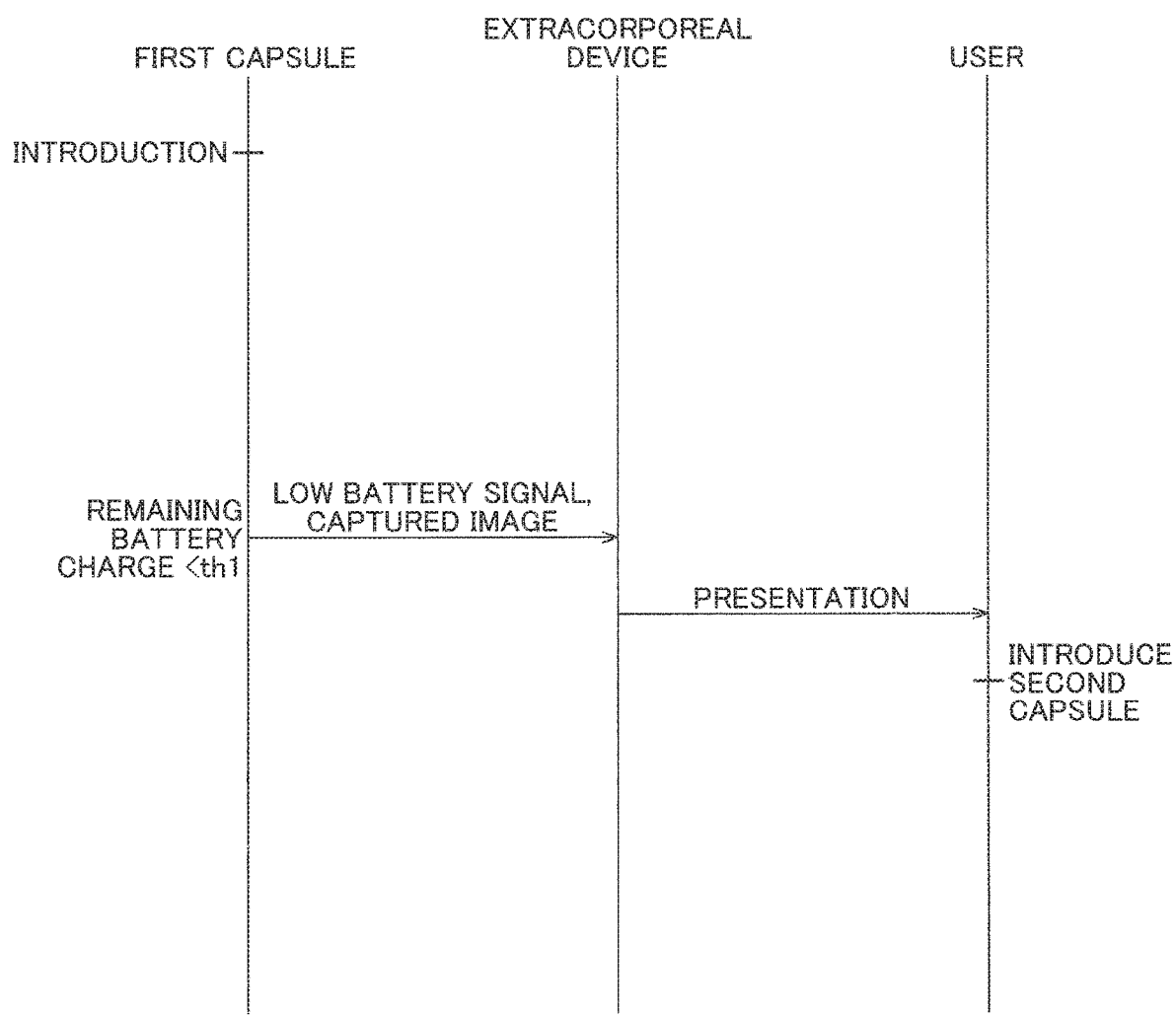
FIG. 16 illustrates an operation example according to the third embodiment.

FIG. 16 illustrates an operation example according to the third embodiment. The description is given based on a case where the large intestine is examined with the capsule endoscope. The power runs out in about 10 hours after the first capsule endoscope device 100 has been introduced into the patient's body. Thus, the information transmission section 104 wirelessly transmits the low battery signal to the information reception and transmission section 206 in the extracorporeal device 200 before (for example 15 minutes before) the power down, based on control performed by the control section 110.

The presentation section 220 issues information (notification) indicating that the low battery signal has been received from the first capsule endoscope device 100. For example, the presentation section 220 includes a light emitting section or a speaker and issues the notification to the user with light emitted from the light emitting section and warning sound from the speaker.

Upon receiving the notification, the physician checks the captured images before and after the received timing, to check the located position of the first capsule endoscope device 100 in the patient's body. When the first capsule endoscope device 100 has not reached the large intestine, or is in the large intestine but is unlikely to be excreted from the living body before the battery runs out, the physician introduces the second capsule endoscope device 300 into the patient's body.

Alternatively, the extracorporeal device 200 may estimate the located position of the first capsule endoscope device 100 through image recognition as in the second embodiment. In this configuration, the extracorporeal device 200 notifies the physician of the located position of the first capsule endoscope device 100 at the timing where the low battery signal has been received from the first capsule endoscope device 100. For example, the presentation section 220 may include light emitting sections corresponding the various parts of the digestive tract, and one of the light emitting sections corresponding to the part where the device is determined to be located may emit light. Alternatively, the presentation section 220 may include a display device such as a liquid crystal display, and the located position may be presented with an image indicating the position displayed.

Specifically, the small intestine of a human being has a length in a range between five to six meters, and has villi distributed therein. The other digestive organs such as the stomach and the large intestine have no villi. Thus, the located position of the first capsule endoscope device 100 may be estimated using an image recognition technique, with classification items "include villi" and "no villi" set. When the information reception and transmission section 206 in the extracorporeal device 200 receives the low battery signal from the first capsule endoscope device 100, the analysis section 204 reads the images captured by the first capsule endoscope device 100 around the received timing from the image storage section 203, to perform the classification of the captured images, based on control performed by the control section 207. When a predetermined number of images or more is determined to "include villi", the first capsule endoscope device 100 can be determined to be still in the small intestine. Thus, the physician is notified of the information, and makes the patient swallow the second capsule endoscope device 300.

Alternatively, the captured image transmitted to the extracorporeal device 200 after the first capsule endoscope device 100 has been introduced into the patient's body may be classified. When the information reception and transmission section 206 in the extracorporeal device 200 receives the low battery signal from the first capsule endoscope device 100, the control section 207 calculates a time period T2 between the timing at which the last image determined to "include villi" by the analysis section 204 has been captured and the timing at which the low battery signal has been received by the information reception and transmission section 206. Specifically, T2 represents a time period between the timing at which the first capsule endoscope device 100 enters the large intestine and the timing at which the low battery signal is transmitted. The presentation section 220 presents this time period T2 to the physician. For example, an average staying time period of the capsule main body in the large intestine is assumed to be three hours. When presented T2 indicates an hour, the physician can determine that the first capsule endoscope device 100 has entered the large intestine but cannot capture the images over the entire large intestine area. In such a case, the physician introduces the second capsule endoscope device 300 into the patient.

When the small intestine is examined, the physician determines not to introduce the second capsule endoscope device 300 into the patient's body in the following case. Specifically, this determination is made when the information reception and transmission section 206 in the extracorporeal device 200 receives the low battery signal from the first capsule endoscope device 100 and the analysis section 204 determines that the first capsule endoscope device 100 has already entered the large intestine area by using the image recognition technique. For example, the presentation section 220 presents the result of the analysis by the analysis section 204 when the low battery signal is received, by using the light emitting section, the display device, or the like, to the physician.

The advancing movement of the first capsule endoscope device 100 is largely affected by the amount of debris in the patient's body. Specifically, when there is a large amount of debris (especially in the large intestine area), the first capsule endoscope device 100 moves slow and thus stays long in the patient's body. In such a case, the images captured by the first capsule endoscope device 100 are classified using the image recognition technique with classification items "include debris" and "no debris" set. When the large intestine is examined, the physician determines that the first capsule endoscope device 100 is likely to have battery exhausted before being excreted from the living body and introduces the second capsule endoscope device 300 into the patient's body under the following condition. Specifically, this determination may be made when the first capsule endoscope device 100 has not been excreted from the living body before a predetermined time period (for example, five hours. This time period may be set from experience based on conventional cases) elapses after being introduced into the patient's body, and when a percentage of (the number of) the captured images classified as "include debris" in all the captured images is higher than a predetermined threshold value. For example, the presentation section 220 presents the time elapsed after the first capsule endoscope device 100 has been introduced into the patient's body and the percentage of the captured images classified as "include debris" in all the captured images, to the physician.

The first capsule endoscope device 100 moves differently (advances at different speeds) in the living body among patients. Generally, the first capsule endoscope device 100 moving fast is likely to be excreted earlier from the living body, and the first capsule endoscope device 100 moving slow is likely to be excreted later from the living body. The timing at which the second capsule endoscope device 300 is introduced may be measured based on this rule.

A description is given with examination on the large intestine as an example. Based on the images captured by the first capsule endoscope device 100 in time series, similarity between consecutive images is calculated to measure the movement of the first capsule endoscope device 100. For example, a Sum of Absolute Difference (SAD) value is calculated with the following Formula (2). Similarity between two captured images is determined to be high with a SAD value closer to 0. The SAD value is calculated by the image processing section 202 for example. Alternatively, an unillustrated movement amount calculation section may be provided.

[Formula 2]

$$isad = \sum_{j=0}^{N-1} \sum_{i=0}^{M-1} (|I(i,j) - I'(i,j)|) \quad (2)$$

In the formula, isad represents the SAD value, i represents a horizontal axis coordinate of a two-dimensional captured image, j represents a vertical axis coordinate of the two-dimensional image, M represents a lateral length of the captured image, N represents a longitudinal length of the captured image, I (i,j) represents a pixel value (luminance value) at coordinates (i,j) in the current captured image, and I' (i,j) represents a pixel value (luminance value) at the coordinates (i,j) in a past captured image.

When the SAD value isad is larger than the predetermined threshold value, the first capsule endoscope device 100 is determined to be moving (or moving fast), whereby a flag "moving" is stored. When the SAD value isad is not larger than the predetermined threshold value, the first capsule endoscope device 100 is determined to be not moving (or moving slow), whereby a flag "not moving" is stored. In this manner, movement information on each captured image is calculated and stored. For example, the flag is stored in an unillustrated storage section.

Then, the physician determines that the first capsule endoscope device 100 is likely to have the battery exhausted before being excreted from the living body, and introduces the second capsule endoscope device 300 into the patient's body under the following condition. Specifically, the determination may be made when the first capsule endoscope device 100 has not been excreted from the living body before a predetermined time period (for example, five hours. This time period may be set from experience based on conventional cases) elapses after being introduced into the patient's body, and when the percentage of (the number of) the captured images determined to have "no movement" in all the captured images is higher than a predetermined threshold value. For example, the presentation section 220 presents the time elapsed after the first capsule endoscope device 100 has been introduced into the patient's body and the percentage of the captured images determined to have "no movement" in all the captured images is higher than a predetermined threshold value (or information indicating whether or not the percentage is higher than the threshold value), to the physician.

In this manner, the position of the first capsule endoscope device 100 in the living body is estimated, based on the time elapsed after the first capsule endoscope device 100 has been introduced into the patient's body, classification information (based on villi, debris, or the like) obtained by an image recognition technique, correlation between images (movement amount), and the like. Then, whether or not to introduce the second capsule endoscope device 300 into the patient's body is adaptively determined with the remaining battery charge recognized. When the first capsule endoscope device 100 is determined not to have sufficient remaining battery charge to capture the images over the entire examination target area, the second capsule endoscope device 300 is introduced into the patient's body to examine the living body of a single patient by the relay system. On the other hand, when the first capsule endoscope device 100 is determined to have sufficient remaining battery charge to capture the images over the entire examination target area, the second capsule endoscope device 300 is not introduced into the patient's body.

The first capsule endoscope device 100 might have the power expired while stopping advancing at a certain location (for example, the colon having an S shape) in the living body. In this situation, the second capsule endoscope device 300 may be introduced only to have the power expired while stopping advancing at the same location as the first capsule endoscope device 100.

The following modifications may be implemented for such a situation. Specifically, when the first capsule endoscope device 100 has the battery exhausted in a state of being stopped advancing at a certain location in the living body (for example, the colon having an S shape), the second capsule endoscope device 300 is not introduced into the living body until the first capsule endoscope device 100 is excreted from the living body. The physician may wait until the first capsule endoscope device 100 is excreted from the living body naturally through intestinal peristalsis. Alternatively, the excretion of the first capsule endoscope device 100 from the living body may be facilitated with the physician introducing a booster, peristaltic accelerator, or the like into the patient's body, with the patient exercising, or with treatment such as massages. After the first capsule endoscope device 100 has been excreted from the living body, the second capsule endoscope device 300 is introduced into the living body at the timing determined by the physician.

The imaging by the second capsule endoscope device 300 may be controlled by the method described in the first and the second embodiments (using image recognition or timer, for example). Specifically, the second capsule endoscope device 300 starts capturing images (or captures images with the frame rate switched to high), after being determined to have reached the location where the power of the first capsule endoscope device 100 has run out. The second capsule endoscope device 300 may start capturing images immediately after being determined to have reached the location. Alternatively, the physician may be notified that the location has been reached, and adaptively control the imaging by the second capsule endoscope device 300 in accordance with the situation determined. Thus, a plurality of capsule main bodies may be prevented from running out of power while stopping at the same location.

The endoscope system according to the third embodiment described above includes: the first capsule endoscope device 100; the second capsule endoscope device 300; and the processing device that performs a process of presenting introduction determination information for determining whether or not to introduce the second capsule endoscope device 300 into the living body or determining an introduction timing, based on the first information on the first capsule endoscope device 100 introduced into the living body before the second capsule endoscope device 300 is introduced.

With this configuration, the physician can receive the introduction determination information thus presented, and determine whether or not to introduce the second capsule endoscope device 300 into the living body or determine the introduction timing, based on the information. Thus, the imaging can be performed by the relay system with the second capsule endoscope device introduced into the patient as appropriate.

The processing device according to the third embodiment corresponds to the extracorporeal device 200 in FIG. 15. However, this should not be construed in a limiting sense, and the processing device may be incorporated in the second capsule endoscope device 300, as described later with reference to FIG. 17. The introduction determination information may be any information with which the physician, who has received the information, can determine whether or not to introduce the second capsule endoscope device 300 into the living body or determine an introduction timing. For example, blinking of a lamp, warning sound, vibration, displayed image, or the like indicating that the capsule needs to be introduced or that the introduction timing has arrived may be employed. In this configuration, the physician who has received the information may immediately introduce the capsule endoscope device. Alternatively, an image or the like for notifying the physician of information indicating whether or not to introduce the second capsule endoscope device 300 or the introduction timing may be displayed. In this case, the physician that has received the information may introduce the capsule endoscope device based on the result or the timing indicated (estimated) by the information. For example, the presentation process may be performed through various methods with which information can be presented (notified) from a device to people, with the blinking of a lamp, warning sound, vibration, displayed image, or the like.

The first information according to the present embodiment corresponds to the remaining battery charge information on the first capsule endoscope device 100.

When the first capsule endoscope device 100 with low remaining battery charge (that is, when the imaging by the first capsule endoscope device 100 is almost disabled) has not been excreted from the living body, it can be determined that the first capsule endoscope device 100 is less likely to be capable of solely completing the imaging. In this manner, the physician can determine whether or not to introduce the second capsule endoscope device 300 or determine the introduction timing, based on the remaining battery charge.

The first information according to the present embodiment corresponds to information on the time elapsed after the first capsule endoscope device 100 has been introduced into the living body.

The time period between the timing at which the operation by the capsule endoscope device starts and the timing at which the imaging is disabled is roughly determined by the specification (for example, based on battery capacity and the current consumption of the capsule endoscope device). Thus, when the first capsule endoscope device 100 has not been excreted from the living body before the time period elapses, it can be determined that the first capsule endoscope device 100 is less likely to be capable of solely completing the imaging. In this manner, the physician can determine whether or not to introduce the second capsule endoscope device 300 or determine the introduction timing, based on the information indicating the time elapsed after the first capsule endoscope device 100 has been introduced into the living body.

The introduction determination information according to the present embodiment corresponds to information indicating whether the imaging by the first capsule endoscope device 100 has been completed over the entire target range of the living body.

For example, if the target range is the small intestine or the large intestine, whether the imaging has been successfully completed over the entire small intestine or the large intestine can be determined based on the last image captured by the first capsule endoscope device 100 (or slightly before the battery runs out). For example, the introduction determination information may be information on the part determined by the processing device through the image recognition, or may be the captured image itself. With these pieces of information, the physician can determine whether or not to introduce the second capsule endoscope device 300 or determine the introduction timing.

The introduction determination information according to the present embodiment corresponds to an image captured by the first capsule endoscope device 100.

As described above, the physician can determine whether or not the first capsule endoscope device 100 has successfully completed the imaging of the target range inside the living body, based on an image captured by the first capsule endoscope device 100 (in particular, the last image captured by the first capsule endoscope device 100 (or captured slightly before the battery runs out)). Thus, the physician can determine whether or not to introduce the second capsule endoscope device 300 or determine the introduction timing, based on the captured image.

4. Modifications

Figure 17:
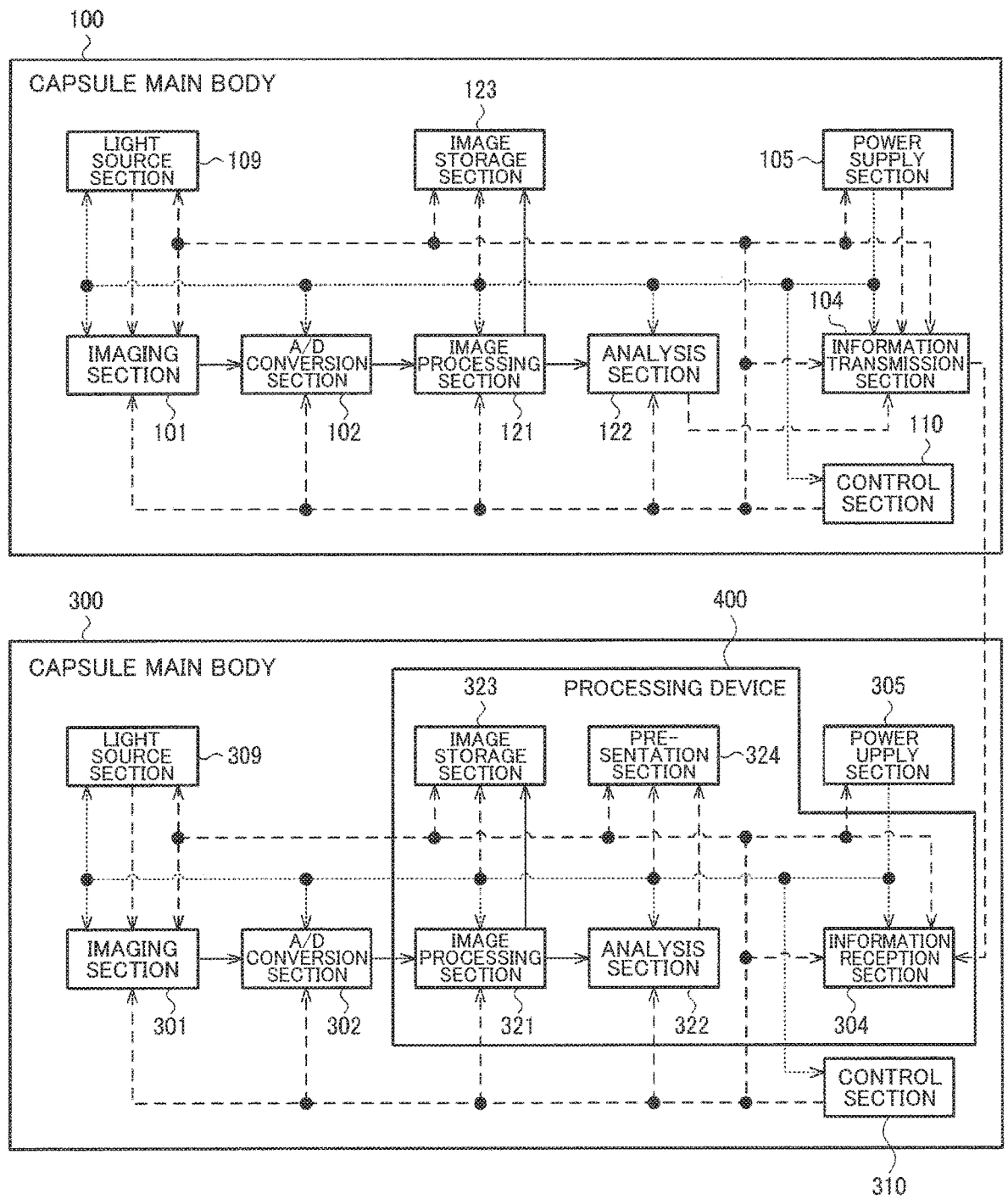
FIG. 17 illustrates an example of a configuration of an endoscope system according to a modification.

FIG. 17 illustrates an example of a configuration of an endoscope system according to a modification. The endoscope system includes the first capsule endoscope device 100 and the second capsule endoscope device 300. The first capsule endoscope device 100 includes the imaging section 101, the A/D conversion section 102, the information transmission section 104 (first communication device), the power supply section 105, the light source section 109, the control section 110 (first controller), the image processing section 121, the analysis section 122, and the image storage section 123 (first memory). The second capsule endoscope device 300 includes the imaging section 301, the A/D conversion section 302, the power supply section 305, the light source section 309, the control section 310 (second controller), and a processing device 400. The processing device 400 includes the image processing section 321, the analysis section 322, an image storage section 323 (second memory), the presentation section 324 (notification section), and the information reception section 304 (second communication device). The components that have already been described are denoted with the same reference numerals, and the description thereof will be omitted as appropriate.

In this modification, the processing device 400 is in the second capsule endoscope device 300, and presents (notifies) a timing for introducing the second capsule endoscope device 300 to the physician upon receiving the low battery signal from the first capsule endoscope device 100. For example, the processing device 400 may include a CPU, an MPU, an ASIC, or the like.

In the first capsule endoscope device 100, the image processing section 121 executes image processing on a Bayer image to generate an RGB image. The image storage section 123 stores the RGB image as a captured image. The analysis section 122 corresponds to the classification section 401 and the storage section 404 in the analysis section 204 in FIG. 6. Specifically, the analysis section 122 classifies the captured images stored in the image storage section 123, based on classification items learned in advance (for example classification based on the density of the villi, classification based on the type of the mucous membrane, or the like). The information transmission section 104 wirelessly transmits the classification result to the information reception section 304 in the second capsule endoscope device 300. The information transmission section 104 wirelessly transmits the low battery signal to the information reception section 304. For example, the classification result at the timing at which the remaining battery charge drops to or below the predetermined amount (the timing at which the low battery signal is transmitted) is transmitted as the classification result.

In the second capsule endoscope device 300, when the information reception section 304 receives the low battery signal from the first capsule endoscope device 100, the presentation section 324 presents (notifies) information indicating that the signal has been received, by using light emitted from the light emitting section or a warning sound emitted from the speaker, to the physician, for example. Alternatively, if it is determined from the received classification result that the first capsule endoscope device 100 is incapable of capturing the images entirely over the target range when the low battery signal is received (when the classification result at the timing when the low battery signal is received indicates the small intestine), the presentation section 324 may present this information to the physician. Then, the physician introduces the second capsule endoscope device 300 into the patient's body, based on the information thus presented by the presentation section 324.

When the second capsule endoscope device 300 is introduced, the image processing section 321 executes image processing on a Bayer image to generate an RGB image. The image storage section 323 stores the RGB image as a captured image. The analysis section 322 corresponds to the classification section 402, the analysis determination section 403 and the storage section 404 in the analysis section 204 in FIG. 6. Specifically, the analysis section 322 classifies the captured images stored in the image storage section 323, based on classification items learned in advance (for example classification based on the density of the villi, classification based on the type of the mucous membrane, or the like). The classification result is compared with the classification result received by the information reception section 304 from the first capsule endoscope device 100. When the classification results match, the second capsule endoscope device 300 can be determined to have reached the position where the remaining battery charge of the first capsule endoscope device 100 has dropped to or below the predetermined amount. When the analysis section 322 determines that the classification results match, the control section 310 causes the imaging section 301 to start the imaging (or switches the frame rate from the low frame rate to the high frame rate).

Although the embodiments to which the invention is applied and the modifications thereof have been described in detail above, the invention is not limited to the embodiments and the modifications thereof, and various modifications and variations may be made without departing from the scope of the invention. A plurality of elements described above in connection with the embodiments and the modifications thereof may be appropriately combined to implement various configurations. For example, some of the elements described above in connection with the embodiments and the modifications thereof may be omitted. Some of the elements described above in connection with the embodiments and the modifications thereof may be appropriately combined. Specifically, various modifications and applications are possible without materially departing from the novel teachings and advantages of the invention. Any term cited with a different term having a broader meaning or the same meaning at least once in the specification and the drawings can be replaced by the different term in any place in the specification and the drawings.

What is claimed is:

1. An endoscope system comprising:
a first capsule endoscope device; and
a second capsule endoscope device,
the first capsule endoscope device being configured to be introduced into a living body before the second capsule endoscope device is introduced into the living body, and the first capsule endoscope device including:
a first image sensor; and
a first processor that controls an imaging operation of the first image sensor,
the second capsule endoscope device including:
a second image sensor; and
a second processor that performs control of an imaging operation of the second image sensor based on first information on the first capsule endoscope device,
the control performed by the second processor including an increase in a power consumption of the second capsule endoscope device, and
the first information including at least one of (i) information on a remaining battery charge of the first capsule endoscope device, (ii) an image captured by the first capsule endoscope device, (iii) information on a time during which the first capsule endoscope device is within the living body, and (iv) position information indicating a position of the first capsule endoscope device in the living body.

2. The endoscope system as defined in claim 1, the control performed by the second processor including starting the imaging operation of the second image sensor or switching a frame rate of the imaging operation of the second image sensor, in response to a trigger signal based on the first information.

3. The endoscope system as defined in claim 2, further comprising a processing device that outputs the trigger signal upon receiving the first information, the second processor performing the control of the imaging operation when the second processor receives the trigger signal from the processing device.

4. The endoscope system as defined in claim 3, the first processor performing a first communication process of transmitting the information on the remaining battery charge of the first capsule endoscope device, the processing device outputting the trigger signal when a predetermined period of time elapses after the remaining battery charge drops to or below a predetermined amount.

5. The endoscope system as defined in claim 4, the predetermined period of time corresponding to time difference between introduction of the first capsule endoscope device into the living body and introduction of the second capsule endoscope device into the living body.

6. The endoscope system as defined in claim 3, the first processor performing a first communication process of transmitting the information on the remaining battery charge of the first capsule endoscope device and an image captured by the first capsule endoscope device,
the processing device acquiring the position information indicating the position of the first capsule endoscope device in the living body at a timing where the remaining battery charge drops to or below the predetermined amount, based on the captured image, and
the processing device outputting the trigger signal when a match between a position of the second capsule endoscope device in the living body and the position indicated by the position information is determined to have occurred, based on images captured by the second capsule endoscope device.

7. The endoscope system as defined in claim 6, the processing device outputting the trigger signal when the match is determined to have occurred within a predetermined range of time, based on a predetermined time period after the remaining battery charge has dropped to or below the predetermined amount.

8. The endoscope system as defined in claim 3, the processing device being an extracorporeal device, and
the second processor performing a second communication process of receiving the trigger signal.

9. The endoscope system as defined in claim 1, further comprising a processing device that performs a process of presenting introduction determination information for determining whether or not to introduce the second capsule endoscope device into the living body or determining an introduction timing, based on the first information.

10. A capsule endoscope device comprising:
an image sensor; and
a processor that controls an imaging operation of the image sensor,
the capsule endoscope device being settable to be in a first operation mode and settable to be in a second operation mode,
the processor performing, when the capsule endoscope device is set to be in the second operation mode, control of the image operation of the image sensor, based on first information on another capsule endoscope device that has been introduced into a living body before the capsule endoscope device set to be in the second operation mode is introduced into the living body, and that has been set to be in the first operation mode,
the control performed by the processor including an increase in a power consumption of the capsule endoscope device, and
the first information including at least one of (i) information on a remaining battery charge of the another capsule endoscope device, (ii) an image captured by the another capsule endoscope device, (iii) information on a time during which the another capsule endoscope device is within the living body, and (iv) position information indicating a position of the another capsule endoscope device in the living body.

11. An endoscope system comprising:
a first capsule endoscope device;
a second capsule endoscope device; and
a processing device that performs a process of presenting introduction determination information for determining whether or not to introduce the second capsule endoscope device into a living body or determining an introduction timing, based on first information on the first capsule endoscope device that has been introduced into the living body before the second capsule endoscope device is introduced into the living body,
the first information including at least one of (i) information on a remaining battery charge of the first capsule endoscope device and (ii) information on a time elapsed after the first capsule endoscope device has been introduced into the living body.

12. The endoscope system as defined in claim 11, the introduction determination information indicating whether or not the first capsule endoscope device has successfully completed imaging of a target range in the living body.

13. The endoscope system as defined in claim 11, the introduction determination information including an image captured by the first capsule endoscope device.

14. A method for operating an endoscope system, the method comprising:
introducing a first capsule endoscope device into a living body, the first capsule endoscope device including a first image sensor and a first processor that controls an imaging operation of the first image sensor; and
introducing a second capsule endoscope device into the living body, the second capsule endoscope device including a second image sensor and a second processor that performs control of an imaging operation of the second image sensor based on first information on the first capsule endoscope device,
the control performed by the second processor including an increase in a power consumption of the second capsule endoscope device, and
the first information including at least one of (i) information on a remaining battery charge of the first capsule endoscope device, (ii) an image captured by the first capsule endoscope device, (iii) information on a time during which the first capsule endoscope device is within the living body, and (iv) position information indicating a position of the first capsule endoscope device in the living body.

\* \* \* \* \*